(12) United States Patent
Futo et al.

(10) Patent No.: US 9,617,303 B2
(45) Date of Patent: Apr. 11, 2017

(54) SUSTAINED-RELEASE COMPOSITION AND METHOD FOR PRODUCING THE SAME

(71) Applicant: Takeda Pharmaceutical Company Limited, Osaka-shi, Osaka (JP)

(72) Inventors: Tomomichi Futo, Osaka (JP); Kazuhiro Saito, Osaka (JP); Tetsuo Hoshino, Osaka (JP); Masuhisa Hori, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 86 days.

(21) Appl. No.: 14/547,467

(22) Filed: Nov. 19, 2014

(65) Prior Publication Data

US 2015/0080322 A1    Mar. 19, 2015

Related U.S. Application Data

(62) Division of application No. 12/312,751, filed as application No. PCT/JP2007/074617 on Dec. 17, 2007, now Pat. No. 8,921,326.
(Continued)

(51) Int. Cl.
*C07K 7/06* (2006.01)
*A61K 9/00* (2006.01)
(Continued)

(52) U.S. Cl.
CPC .............. *C07K 7/06* (2013.01); *A61K 9/0019* (2013.01); *A61K 9/19* (2013.01); *A61K 9/5031* (2013.01);
(Continued)

(58) Field of Classification Search
CPC .......... C07K 7/06; A61K 9/0019; A61K 9/19; A61K 9/5031; A61K 31/55; A61K 9/5089; A61K 38/00
See application file for complete search history.

(56) References Cited

U.S. PATENT DOCUMENTS

| 3,297,033 A | 1/1967 | Schmitt et al. |
| 3,565,869 A | 2/1971 | DeProspero |

(Continued)

FOREIGN PATENT DOCUMENTS

| EP | 0 145 240 A2 | 6/1985 |
| EP | 0 190 833 | 8/1986 |

(Continued)

OTHER PUBLICATIONS

Beck et al., "Systemic and local delivery of contraceptive steroids using biodegradable microcapsules," Progress in Contraceptive Delivery Systems, 1980, vol. 1, 63-81.
(Continued)

*Primary Examiner* — Trevor Love
(74) *Attorney, Agent, or Firm* — Foley & Lardner LLP

(57) ABSTRACT

Sustained-release compositions wherein a water-soluble physiologically active peptide is substantially uniformly dispersed in a microcapsule comprised of a lactic acid polymer or a salt thereof, and the physiologically active substance is contained in an amount of 15 to 35 wt/wt % to the total microcapsules and weight-average molecular weight (Mw) of the lactic acid polymer is about 11,000 to about 27,000, which is characterized by having a high content of the physiologically active substance, and suppression of the initial excessive release within one day after the administration and a stable drug sustained-release over a long period of time, and method for producing the same.

27 Claims, 5 Drawing Sheets

Related U.S. Application Data

(60) Provisional application No. 60/875,364, filed on Dec. 18, 2006, provisional application No. 60/917,401, filed on May 11, 2007.

(51) Int. Cl.
*A61K 9/19* (2006.01)
*A61K 9/50* (2006.01)
*A61K 31/55* (2006.01)
*A61K 38/00* (2006.01)

(52) U.S. Cl.
CPC ............ *A61K 9/5089* (2013.01); *A61K 31/55* (2013.01); *A61K 38/00* (2013.01)

(56) References Cited

U.S. PATENT DOCUMENTS

| | | |
|---|---|---|
| 3,755,558 A | 8/1973 | Scribner |
| 3,773,919 A | 11/1973 | Boswell et al. |
| 3,839,297 A | 10/1974 | Wasserman et al. |
| 3,890,283 A | 6/1975 | Casey et al. |
| 3,912,692 A | 10/1975 | Casey et al. |
| 4,249,531 A | 2/1981 | Heller et al. |
| 4,258,063 A | 3/1981 | Chun et al. |
| 4,273,920 A | 6/1981 | Nevin |
| 4,479,911 A | 10/1984 | Fong |
| 4,539,981 A | 9/1985 | Tunc |
| 4,605,730 A | 8/1986 | Shalaby et al. |
| 4,652,441 A | 3/1987 | Okada et al. |
| 4,677,191 A | 6/1987 | Tanaka et al. |
| 4,728,721 A | 3/1988 | Yamamoto et al. |
| 4,767,628 A | 8/1988 | Hutchinson |
| 4,801,739 A | 1/1989 | Franz et al. |
| 4,849,228 A | 7/1989 | Yamamoto et al. |
| 4,954,298 A | 9/1990 | Yamamoto et al. |
| 5,004,602 A | 4/1991 | Hutchinson |
| 5,366,734 A | 11/1994 | Hutchinson |
| 5,480,656 A | 1/1996 | Okada et al. |
| 5,540,937 A | 7/1996 | Billot et al. |
| 5,575,987 A | 11/1996 | Kamei et al. |
| 5,585,460 A | 12/1996 | Yamada et al. |
| 5,594,091 A | 1/1997 | Igari et al. |
| 5,611,971 A | 3/1997 | Maedera et al. |
| 5,665,394 A | 9/1997 | Igari et al. |
| 5,763,513 A | 6/1998 | Suzuki et al. |
| 5,851,451 A | 12/1998 | Takechi et al. |
| 5,922,682 A | 7/1999 | Brich et al. |
| 5,945,126 A | 8/1999 | Thanoo et al. |
| 5,980,947 A | 11/1999 | Yamakawa et al. |
| 6,045,830 A | 4/2000 | Igari et al. |
| 6,113,943 A | 9/2000 | Okada et al. |
| 6,190,700 B1 | 2/2001 | Okada et al. |
| 6,353,086 B1 | 3/2002 | Kolstad et al. |
| 6,361,798 B1 | 3/2002 | Thanoo et al. |
| 6,528,093 B1 | 3/2003 | Kamei et al. |
| 6,565,874 B1 | 5/2003 | Dunn et al. |
| 6,699,500 B2 | 3/2004 | Okada et al. |
| 6,740,634 B1 | 5/2004 | Saikawa et al. |
| 6,756,472 B1 | 6/2004 | Hata et al. |
| 7,048,947 B2 | 5/2006 | Kamei et al. |
| 7,265,157 B1 | 9/2007 | Igari et al. |
| 7,429,559 B2 | 9/2008 | Yamamoto et al. |
| 2004/0241229 A1 | 12/2004 | Yamamoto et al. |
| 2005/0042294 A1 | 2/2005 | Thanoo et al. |
| 2005/0064039 A1 | 3/2005 | Futo et al. |
| 2005/0079224 A1 | 4/2005 | Rickey et al. |
| 2005/0152911 A1 | 7/2005 | Hardy |
| 2008/0118545 A1 | 5/2008 | Futo et al. |

FOREIGN PATENT DOCUMENTS

| | | |
|---|---|---|
| EP | 0 442 671 A2 | 8/1991 |
| EP | 0 202 065 B1 | 4/1993 |
| EP | 0 586 238 A2 | 3/1994 |
| EP | 0 052 510 B2 | 10/1994 |
| EP | 0 668 073 A2 | 8/1995 |
| EP | 0 839 525 A1 | 5/1998 |
| EP | 1 048 301 A1 | 11/2000 |
| EP | 1 158 014 A1 | 11/2001 |
| EP | 1 197 208 A1 | 4/2002 |
| EP | 0 058 481 B2 | 5/2003 |
| EP | 1 310 517 A1 | 5/2003 |
| EP | 1 532 985 A1 | 5/2005 |
| EP | 1 310 517 B1 | 4/2006 |
| GB | 2 145 422 A | 3/1985 |
| JP | 6-78425 B2 | 10/1994 |
| JP | 7-278277 A | 10/1995 |
| JP | 7-273447 A | 10/1998 |
| JP | 11-269094 A | 10/1999 |
| WO | WO 95/15767 | 6/1995 |
| WO | WO 91/12882 A1 | 10/1995 |
| WO | WO 98/32423 A1 | 7/1998 |
| WO | WO 99/12549 A2 | 3/1999 |
| WO | WO 99/15154 A1 | 4/1999 |
| WO | WO 99/44590 A1 | 9/1999 |
| WO | WO 00/35990 A1 | 6/2000 |
| WO | WO 01/05380 A1 | 1/2001 |
| WO | WO 01/10414 A1 | 2/2001 |
| WO | WO 02/12369 A1 | 2/2002 |
| WO | WO 02/43766 A1 | 6/2002 |
| WO | WO 02/47722 A1 | 6/2002 |
| WO | WO 03/002092 A2 | 1/2003 |
| WO | WO 2005/007122 A2 | 1/2005 |
| WO | WO 2005/009357 A2 | 2/2005 |
| WO | WO2006/004167 A1 | 1/2006 |
| WO | WO 2006/039336 A2 | 4/2006 |
| WO | WO 2006/053175 A2 | 5/2006 |

OTHER PUBLICATIONS

Bittner et al., "Bovine serum albumin loaded poly(lactide-co-glycolide) microspheres: the influence of polymer purity on particle characteristics," J. Microencapsulation, 1998, 15(4):495-514.

Braun et al., Praktikal Macromolecular Organic Chemistry, 1966, any edition, 57-59, with English translation.

Brock, Thomas D., "Membrane Filtration, A User's Guide and Reference Manual," Science Tech, Inc., 1983, 290-291.

Collins et al., "Isolation and Purification of Polymer," Experiments in Polymer Science, 1973, pp. 62-69.

Eisenbach, Prof. Dr. Claus D., Expert Opinion of Apr. 4, 2006 in EP 1 310 517, 44 pages.

Encyclopedic Handbook of Biomaterials and Bioengineering, Part A: Materials, vol. 2, 1995, 1014-1054.

Jeyanthi et al., "Effect of processing parameters on the properties of peptide-containing PLGA microspheres," J. Microencapsulation, 1997, 14(2):163-174.

Kostanski et al., "Preparation, Characterization, and In Vitro Evaluation of 1- and 4-Month Controlled Release Orntide PLA and PLGA Microspheres," Pharmaceutical Development and Technology, 2000, 5(4):585-596.

Kulkarni et al., "Biodegradable Poly(lactic acid) Polymers," J. Biomed. Mater. Res., 1971, 5, 169-181.

Miller et al., "Degradation Rates of Oral Resorbable Implants (Polylactates and Polyglycolates): Rate Modification with Changes in PLA/PGA Copolymer Ratios," J. Biomed. Mater. Res., 1977, 11, 711-719.

Mohr et al., "Gamma irradiation for terminal sterilization of 17β-estradiol loaded poly-(D,L-lact de-co-glycolide) microparticles," Journal of Controlled Release, 1999, 61:203-217.

Niwa et al., "Preparations of biodegradable nanospheres of water-soluble and insoluble drugs with D,L-lactide/glycolide copolymer by a novel spontaneous emulsification solvent diffusion method, and the drug release behavior," Journal of Controlled Release, 1993, 25:89-98.

Ogawa et al. "Controlled-Release of Leuprolide Acetate from Polylactic Acid or Copoly(Lactic/Glycolic) Acid Microcapsules: Influence of Molecular Weight and Copolymer Ratio of Polymer," Chem. Pharm. Bull., 1988, 36(4):1502-1507.

(56) References Cited

OTHER PUBLICATIONS

Okada et al,. "Biodegradable Microspheres in Drug Delivery," Critical Reviews in Therapeutic Drug Carrier Systems, 1995, 12(1)1-99.

Okada et al., "One- and three-month release injectable microspheres of the LH-RH superagonist leuprorelin acetate," Advanced Drug Delivery Reviews, 1997, 28:43-70.

Pitt et al., "Sustained Drug Delivery Systems. I. The Permeability of Poly(ε-Caprolactone), Poly(DL-Lactic Acid), and Their Copolymers," J. Biomed. Mater. Red., 1979, 13, 497-507.

Psychrembel Klinisches Wörterbuch, 1994, 257, Ed., de Gruyter Ed., sections "BnRH" and "GnRH-Agonisten," 3 pages.

Ravivarapu et al., "Polymer and microshere blending to alter the release of a peptide from PLGA microspheres," European Journal of Pharmaceutics and Biopharmaceutics, 2000, 50:263-270.

Rompp Chemie Lexikon, Falbe et al., Ed., 1991 Georg Thieme Verlag, 3107-3108, and English translation (4 pgs.).

Rote Liste, 2000, section 50 036 "Enantone," section 50 038 "Kryptocur," and section 50 039 "Lutrelef," 3 pages.

Ruiz et al., "Influence of Average Molecular Weights of Poly(DL-Lactic Acid-Co-Glycolic Acid) Copolymers 50/50 on Phase Separation and in Vitro Drug Release from Microspheres," Pharmaceutical Research, 1990, 7(9):928-934.

Schartel et al., "Dielectric and thermodynamic properties of biodegradable poly(D,L-lactide-co-glycolide) and the effect of the microencapsulation and release of captopril," J. Microencapsulation, 1997, 14(4):475-488.

Schindler et al., "Biodegradable polymers for sustained drug delivery," Contemporary Topics in Polymer Science, Eli M. Pearce et al., Ed., 1977, 2, pp. 251-289.

Shameem et al., "A Short-term (Accelerated Release) Approach to Evaluate Peptide Release from PLGA Depot Formulations," AAPS Pharmsci., 1999, 1(3)article7:6 pages.

Suzuki et al., "Microencapsulation and Dissolution Properties of a Neuroleptic in a Biodegradable Polymer, Poly(d,l-lactide)," J. Pharm. Science, Jan. 1985, 74(1), 21-25.

Taguchi et al., "Long-term clinical study on TAP-144-SR, an LH-RH agonist depot formulation, in premenopausal patients with advanced or recurrent breast cancer. TAP-144-SR Breast Cancer Study Group," Gan to Kagaku Ryoho, Mar. 1995, 22(4):495-508, with PubMed English Abstract, 15 pages.

Takenaga et al., "A novel sustained-release formulation of insulin with dramatic reduction in initial rapid release," Journal of Controlled Release, 2002, 79:81-91.

The Merck Index, 1989, 11$^{th}$ Ed., entry 4433 "Goserelin," p. 711, 3 pages.

The Merck Index, 1989, 11$^{th}$ Ed., entry 9662 "Triptorelin," pp. 1533-1534, 4 pages.

The Merck Index, 2001, 13$^{th}$ Ed., entry 5478, "Leuprolide," 3 pages.

Vert et al., "Bioresorbable Plastic Materials for Bone Surgery," Macromolecular Biomaterials, 1984, Chapter 6, 119-142.

Vert et al., "Stereoregular Bioresorbable Polyesters for Orthopedic Surgery," Makromol. Chem. Suppl., 1981, 5, 30-41.

Woo et al., "In Vitro Characterization and in Vivo Testosterone Suppression of 6-Month Release Poly(D,L-Lactide) Leuprolide Microspheres," *Pharmaceutical Research* (Apr. 2002), vol. 19, No. 4, pp. 546-550, Plenum Publishing Corporation.

Woodland et al., "Long-Acting Delivery Systems for Narcotic Antagonists," J. Med. Chem., 1973, 16(8), 897-901.

Banga, Ajay K., Ph.D., "Therapeutic Peptides and Proteins: Formulation, Processing, and Delivery Systems," 1995, 192-193.

Luan et al., "Influence of the poly(lactide-co-glycolide) type on the leuprolide release from in situ forming microparticle systems," Journal of Controlled Release, 2006, 110:266-272.

Zolnik et al., "Elevated temperature accelerated release testing of PLGA microspheres," Journal of Controlled Release, 2006, 112:293-300.

Polymer Biomaterials in Solution, as Interfaces and as Solids: A Festschrift Honoring the 60$^{th}$ Birthday of Dr. Allan S. Hoffman, Cooper et al., Eds., 1995, 808-809.

US 9,617,303 B2

SUSTAINED-RELEASE COMPOSITION AND METHOD FOR PRODUCING THE SAME

CROSS-REFERENCE TO RELATED APPLICATIONS

This application is a Divisional of U.S. application Ser. No. 12/312,751, which is the U.S. National Stage application of PCT/JP2007/074617, filed Dec. 17, 2007, which claims priority from U.S. Provisional Application Nos. 60/875,364, filed Dec. 18, 2006, and 60/917,401, filed May 11, 2007.

TECHNICAL FIELD

The present invention relates to a sustained-release preparation of a physiologically active substance, a method for producing the same, and a use as a medicament and the like.

BACKGROUND ART

As a conventional art, for example, Japanese Patent No. 3116311 discloses a microspherical sustained-release preparation comprised of a water-soluble drug such as a physiologically active peptide and a polylactic acid, and as a method for producing the same, there is described a method which comprises dissolving a water-soluble drug such as a physiologically active peptide and a biodegradable polymer in a mixed solvent of a water-immiscible solvent such as dichloromethane and a water-miscible solvent such as ethanol, and adding the solution into water etc. to produce an O/W emulsion, followed by subjecting to an in-water drying method to prepare a sustained-release microcapsule. In addition, Japanese Patent No. 3512408 discloses microspherical microparticles comprising of a water-soluble physiologically active peptide and a polylactic acid or a copolymer of lactic acid and glycolic acid, wherein the release dynamic of the drug is controlled, and as a method for preparing the microparticle, there is described a method which comprises dissolving a polymer in a volatile and water-immiscible solvent, mixing a solution separately prepared by dissolving a water-soluble physiologically active peptide in water-miscible solvent with the above polymer solution, and emulsifying the resulting solution in an aqueous phase containing an emulsifier, followed by removing the solvent from the obtained O/W emulsion to prepare the microspherical microparticles. However, the drug content in each of the sustained-release preparations is about 10% or about 0.1 to 5%, and a sustained-release preparation capable of sustainably releasing the drug over about two months is not described.

Furthermore, Pharmaceutical Research, Vol. 19, No. 4 (April, 2002) discloses a microspherical sustained-release preparation comprised of leuprolide acetate and polylactic acid, and as a process for preparing the preparation, there is described a method which comprises mixing a methanol solution of leuprolide and a dichloromethane solution of polylactic acid, and dispersing the solution in an aqueous solution of polyvinylalcohol, followed by removing the organic solvent to prepare the microspherical sustained-release preparation. The preparation has a characteristic of releasing the drug over a period of 180 to 240 days. However, the drug release is small in amount at the first or second month in the early period of administration after initial burst, and the preparation exhibits a typical triphasic drug release.

DISCLOSURE OF INVENTION

The present invention is intended to provide a novel composition containing a physiologically active substance in high content and capable of achieving a stable releasing rate over a long period of time by suppressing the initial excessive release within one day after the administration and obtaining a stable drug release in the onset part over one day to about one month after the administration, and a method for producing the same.

Also, the present invention is intended to provide a sustained-release preparation which stabilizes blood drug concentration for a long period by the above-described stable drug release over a long period of time.

Furthermore, the present invention is intended to provide a sustained-release preparation in which the volume or weight of the whole sustained-release preparation required for per unit dose of the active ingredient is reduced by increasing a content of a physiologically active substance in the preparation to an elevated amount, that is, increasing the content of the physiologically active substance per unit volume of the sustained-release preparation.

Moreover, the present invention is intended to provide a sustained-release preparation in which a physical burden of patients supposed to be caused by administering a preparation having a bulky unit volume such as pain at the time of administration and induration after the administration is reduced by the preparation having an elevated drug content mentioned above.

In addition, the present invention can achieve at the same time the conflicting objects of a reduction of a physical burden at the time of administration and a reduction of ambulatory burden by decreasing administration frequency with the above-described preparation in which both a stable sustained release over a long period of time and an elevation of drug content are achieved at the same time.

The present inventors have intensively investigated in view of the above-mentioned circumstances, and as a result, have found that a sustained-release preparation comprised of a specific combination or a specific composition and obtained by a specific process for preparation keeps the initial excessive release within one day after the administration at extremely low level and exhibits ideal drug-release characteristic features in the onset part from one day to about one month after administration to a patient, and by using the present sustained-release preparation, an extremely stable blood drug level transition can be achieved over a long period of time due to the inhibition of the initial excessive release within one day after the administration and long-term stable release rate by ideal release dynamics in the onset part in addition to unexpectedly, being able to incorporate a physiologically active substance at a high content.

As a result of a further study based on these knowledge, the inventors have completed the present invention.

That is, the present invention provides:

(1) A sustained-release composition in which a physiologically active substance comprised of a water-soluble physiologically active peptide is substantially uniformly dispersed in a microcapsule comprised of a lactic acid polymer or a salt thereof, wherein said physiologically active substance is contained in an amount of 15 to 35 (weight/weight) % to the total microcapsules and weight-average molecular weight (Mw) of the lactic acid polymer is about 11,000 to about 27,000;

(2) The sustained-release composition according to the above-mentioned (1), wherein the weight-average molecular weight (Mw) of the lactic acid polymer is any one selected from:
(i) about 11,600 to about 20,000 and
(ii) about 19,000 to about 27,000;
(3) The sustained-release composition according to the above-mentioned (2) wherein the weight-average molecular weight (Mw) of the lactic acid polymer is (i) about 11,600 to about 20,000, which comprises maintaining an effective drug blood level over a period of about 60 days to 130 days by in vivo release of the physiologically active substance from the sustained-release composition;
(4) The sustained-release composition according to the above-mentioned (2) wherein the weight-average molecular weight (Mw) of the lactic acid polymer is (ii) about 19,000 to about 27,000, which comprises maintaining an effective drug blood level over a period of about 120 days to 400 days by in vivo release of the physiologically active substance from the sustained-release composition;
(5) The sustained-release composition according to the above-mentioned (1), wherein the physiologically active substance is a LH-RH derivative;
(6) The sustained-release composition according to the above-mentioned (1), wherein the physiologically active substance is a peptide of formula:

5-oxo-Pro-His-Trp-Ser-Tyr-Y-Leu-Arg-Pro-Z wherein, Y represents DLeu, DAla, DTrp, DSer (tBu), D2Nal or DHis (ImBzl) and Z represents NH—$C_2H_5$ or Gly-$NH_2$, or a salt thereof;
(7) The sustained-release composition according to the above-mentioned (1), wherein the physiologically active substance is a peptide of formula:

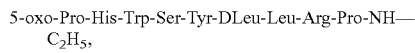
5-oxo-Pro-His-Trp-Ser-Tyr-DLeu-Leu-Arg-Pro-NH—$C_2H_5$, or an acetate thereof;
(8) The sustained-release composition according to the above-mentioned (1), which is characterized in that a content of the contained physiologically active substance is 17 to 26 (weight/weight) % to the total microcapsules;
(9) The sustained-release composition according to the above-mentioned (1) which is obtained by dissolving the lactic acid polymer or the salt thereof in a volatile water-immiscible first solvent to prepare a first solution, dissolving the physiologically active substance comprised of the water-soluble physiologically active peptide in a water-miscible second solvent to prepare a second solution, mixing the resultant first solution and the resultant second solution to prepare a third solution in which the lactic acid polymer or the salt thereof and the physiologically active substance are uniformly dissolved, dispersing the resultant third solution in a fourth solution comprised of an aqueous solution of an emulsifier to prepare an O/W emulsion, and removing the first solvent and the second solvent from the generated microcapsule;
(10) The sustained-release composition according the above-mentioned (9), which is characterized in that a mixed solvent in which a water-miscible third solvent is further added to the first solvent is used as a solvent for dissolving the lactic acid polymer or the salt thereof in the preparation of the first solution;
(11) The sustained-release composition according to the above-mentioned (9), which is characterized in that a controlled temperature of the emulsifying step is adjusted to about 15 to about 35° C. in the step of removing the first solvent and the second solvent from the microcapsule;
(12) The sustained-release composition according the above-mentioned (11), which is characterized in that the temperature control of the emulsifying step is performed by adjusting the temperature of the O/W emulsion to about 15 to 35° C.;
(13) The sustained-release composition according to the above-mentioned (9), wherein the respective temperatures of the third solution and the fourth solution in the preparation of the O/W emulsion are about 15 to about 35° C.;
(14) The sustained-release composition according to the above-mentioned (9), which is characterized in that the step of removing the first solvent and the second solvent from the microcapsule is performed by an in-water drying method;
(15) The sustained-release composition according to the above-mentioned (9), wherein the first solvent is dichloromethane;
(16) The sustained-release composition according to the above-mentioned (9), wherein the second solvent and/or the third solvent is a lower alcohol;
(17) The sustained-release composition according to the above-mentioned (16), wherein the lower alcohol is methanol, ethanol, or propanol;
(18) The sustained-release composition according to the above-mentioned (9), which is characterized in that a volume ratio of the water-immiscible solvent and the water-miscible solvent in the third solution is 35:65 to 55:45;
(19) The sustained-release composition according to the above-mentioned (9), which is characterized in that a polymer concentration in the first solution is about 33 to 45% by weight;
(20) The sustained-release composition according to the above-mentioned (9), which is characterized in that a loading amount of the physiologically active substance in the preparation of the third solution is 17 to 50% by weight;
(21) The sustained-release composition according to the above-mentioned (9), which is characterized in that a content of the contained physiologically active substance is 17 to 26 (weight/weight) % to the total microcapsules;
(22) The sustained-release composition according to the above-mentioned (21), which is characterized in that a loading amount of the physiologically active substance in the preparation of the third solution is 19 to 38% by weight;
(23) The sustained-release composition according to the above-mentioned (21), which is characterized in that a loading amount of the physiologically active substance in the preparation of the third solution is 20 to 23% by weight;
(24) The sustained-release composition according to the above-mentioned (1), which is characterized in that the sustained-release composition further contains a fatty acid;
(25) The sustained-release composition according to the above-mentioned (24), wherein the fatty acid is at least one selected from stearic acid, benzoic acid, hydroxynaphthoic acid, and pamoic acid;
(26) The sustained-release composition according to the above-mentioned (24), which is characterized in that a ratio of the fatty acid to the total microcapsules is about 0.01 to about 50% by weight;
(27) The sustained-release composition according to the above-mentioned (24), which is characterized in that an amount of the fatty acid to be added is 0.1 to 10 moles relative to one mole of the water-soluble physiologically active peptide or the salt thereof;
(28) The sustained-release composition according to the above-mentioned (1), which is characterized by being easily-dispersible in a disperse medium;

(29) The sustained-release composition according to the above-mentioned (28), which is characterized by being stable for 24 hours or more after dispersion in the disperse medium;

(30) The sustained-release composition according to the above-mentioned (2) wherein the weight-average molecular weight (Mw) of the lactic acid polymer is (i) about 11,600 to about 20,000, which is characterized in that a ratio of the weight-average molecular weight (Mw) to the number-average molecular weight (Mn) is more than 1.9;

(31) The sustained-release composition according to the above-mentioned (2) wherein the weight-average molecular weight (Mw) of the lactic acid polymer is (ii) about 19,000 to about 27,000, which is characterized in that a ratio of the weight-average molecular weight (Mw) to the number-average molecular weight (Mn) is more than 1.5;

(32) The sustained-release composition according to the above-mentioned (1), which is characterized in that the lactic acid polymer is polylactic acid or polylactide;

(33) The sustained-release composition according to the above-mentioned (1), which is characterized in that the lactic acid polymer is poly-DL-lactic acid or poly-DL-lactide;

(34) The sustained-release composition according to the above-mentioned (1), which is characterized in that the lactic acid polymer is a lactic acid-glycolic acid polymer;

(35) The sustained-release composition according to the above-mentioned (34), which is characterized in that a composition ratio of lactic acid/glycolic acid in the lactic acid-glycolic acid polymer is 60/40 to 99.9/0.1;

(36) The sustained-release composition according to the above-mentioned (1), wherein the lactic acid polymer is a polymer containing a polymer having a molecular weight of 5,000 or less whose content is about 5.0% by weight or less;

(37) The sustained-release composition according to the above-mentioned (1), wherein the lactic acid polymer is a polymer containing a polymer having a molecular weight of 3,000 or less whose content is about 1.5% by weight or less;

(38) The sustained-release composition according to the above-mentioned (1), wherein the lactic acid polymer is a polymer containing a polymer having a molecular weight of 1,000 or less whose content is about 0.1% by weight or less;

(39) The sustained-release composition according to the above-mentioned (2) in which the weight-average molecular weight (Mw) of the lactic acid polymer is (i) about 11,600 to about 20,000, wherein the weight-average molecular weight (Mw) of the lactic acid polymer is 12,000 to 19,000;

(40) The sustained-release composition according to the above-mentioned (2) in which the weight-average molecular weight (Mw) of the lactic acid polymer is (i) about 11,600 to about 20,000, wherein the weight-average molecular weight (Mw) of the lactic acid polymer is 13,000 to 18,000;

(41) The sustained-release composition according to the above-mentioned (2) in which the weight-average molecular weight (Mw) of the lactic acid polymer is (ii) about 19,000 to about 27,000, wherein the weight-average molecular weight (Mw) of the lactic acid polymer is 19,500 to 26,500;

(42) A process for preparation of a sustained-release composition of a microcapsule containing a physiologically active substance at 15 to 35% by weight to the whole microcapsules, comprising steps of:

(i) dissolving a lactic acid polymer or a salt thereof in a volatile water-immiscible first solvent to prepare a first solution, (ii) dissolving the physiologically active substance comprised of a water-soluble physiologically active peptide in a water-miscible second solvent to prepare a second solution, (iii) mixing the resultant first solution and the resultant second solution to prepare a third solution in which the lactic acid polymer or the salt thereof and the physiologically active substance are uniformly dissolved, (iv) dispersing the resultant third solution in a fourth solution comprised of an aqueous solution of a surfactant to prepare an O/W emulsion, and (v) removing the first solvent and the second solvent from the microcapsule by an in-water drying method at a controlled temperature of about 15 to about 35° C.;

(43) The process according to the above-mentioned (42), wherein the weight-average molecular weight (Mw) of the lactic acid polymer is about 11,600 to about 20,000;

(44) The process according to the above-mentioned (42), wherein the weight-average molecular weight (Mw) of the lactic acid polymer is about 19,000 to about 27,000;

(45) The process according to the above-mentioned (42), which is characterized in that a mixed solvent in which a water-miscible third solvent is further added to the first solvent is used as a solvent for dissolving the lactic acid polymer or the salt thereof in the step (i);

(46) The process according to the above-mentioned (42), which is characterized in that the respective temperatures of the third solution and the fourth solution in the preparation of the O/W emulsion are adjusted to about 15 to about 35° C.;

(47) The process for the preparation of a sustained-release composition according to the above-mentioned (42), which is characterized in that a fatty acid or a salt thereof is further added to the first solution and/or the second solution or the third solution;

(48) The process for the preparation of a sustained-release composition according to the above-mentioned (42), which is characterized in that a fatty acid or a salt thereof is dissolved in the second solution;

(49) The process for the preparation of a sustained-release composition according to the above-mentioned (42), which is characterized in that a loading amount of the physiologically active substance in the preparation of the third solution is 17 to 50% by weight;

(50) The process for the preparation of a sustained-release composition according to the above-mentioned (42), which is characterized in that a content of the contained physiologically active substance is 17 to 26 (weight/weight) % to the total microcapsules;

(51) The process for the preparation of a sustained-release composition according to the above-mentioned (50), which is characterized in that a loading amount of the physiologically active substance in the preparation of the third solution is 19 to 38% by weight;

(52) The process for the preparation of a sustained-release composition according to the above-mentioned (50), which is characterized in that a loading amount of the physiologically active substance in the preparation of the third solution is 20 to 23% by weight;

(53) The process for the preparation of a sustained-release composition according to the above-mentioned (42), which is characterized by maintaining an effective drug blood level over a period of about 60 days to 130 days by in vivo release of the physiologically active substance from the sustained-release composition;

(54) The process for the preparation of a sustained-release composition according to the above-mentioned (42), which is characterized by maintaining an effective drug blood level over a period of about 120 days to 400 days by in vivo release of the physiologically active substance from the sustained-release composition;

(55) The sustained-release composition according to the above-mentioned (2) in which the weight-average molecular weight (Mw) of the lactic acid polymer is (i) about 11,600 to about 20,000, which is characterized in that a ratio of a maximum blood concentration of an active ingredient within 24 hours after the administration to an average blood concentration of the active ingredient for a period from 24 hours to one month after the administration is 2 to 50;

(56) The sustained-release composition according to the above-mentioned (2) in which the weight-average molecular weight (Mw) of the lactic acid polymer is (i) about 11,600 to about 20,000, which is characterized in that a ratio of a maximum blood concentration of an active ingredient within 24 hours after the administration to an average blood concentration of the active ingredient for a period from one month to three months after the administration is 20 to 350;

(57) The sustained-release composition according to the above-mentioned (2) in which the weight-average molecular weight (Mw) of the lactic acid polymer is (i) about 11,600 to about 20,000, which is characterized in that area under the blood concentration-time curve (AUC) of an active ingredient within 24 hours after the administration calculated from the blood concentration is 3% to 30% of the whole AUC;

(58) The sustained-release composition according to the above-mentioned (2) in which the weight-average molecular weight (Mw) of the lactic acid polymer is (i) about 11,600 to about 20,000, which is characterized in that area under the blood concentration-time curve (AUC) of an active ingredient for a period from 24 hours to one month after the administration calculated from the blood concentration is 40% to 80% of the whole AUC, and has an excellent sustained-release profile;

(59) The sustained-release composition according to the above-mentioned (2) in which the weight-average molecular weight (Mw) of the lactic acid polymer is (i) about 11,600 to about 20,000, which is characterized in that area under the blood concentration-time curve (AUC) of an active ingredient for a period from one month to three months after the administration is 10% to 35% of the whole AUC, and has an excellent sustained-release profile;

(60) The sustained-release composition according to the above-mentioned (2) in which the weight-average molecular weight (Mw) of the lactic acid polymer is (ii) about 19,000 to about 27,000, which is characterized in that a ratio of a maximum blood concentration of an active ingredient within 24 hours after the administration to an average blood concentration of the active ingredient for a period from 24 hours to one month after the administration is 10 to 90;

(61) The sustained-release composition according to the above-mentioned (2) in which the weight-average molecular weight (Mw) of the lactic acid polymer is (ii) about 19,000 to about 27,000, which is characterized in that a ratio of a blood maximum concentration of an active ingredient within 24 hours after the administration to an average blood concentration of the active ingredient for a period from one month to six months after the administration is 20 to 500;

(62) The sustained-release composition according to the above-mentioned (2) in which the weight-average molecular weight (Mw) of the lactic acid polymer is (ii) about 19,000 to about 27,000, which is characterized in that area under the blood concentration-time curve (AUC) of an active ingredient within 24 hours after the administration calculated from the blood concentration is 1% to 20% of the whole AUC;

(63) The sustained-release composition according to the above-mentioned (2) in which the weight-average molecular weight (Mw) of the lactic acid polymer is (ii) about 19,000 to about 27,000, which is characterized in that area under the blood concentration-time curve (AUC) of an active ingredient for a period from 24 hours to one month after the administration calculated from the blood concentration is 10% to 50% of the whole AUC, and has an excellent sustained-release profile;

(64) The sustained-release composition according to the above-mentioned (2) in which the weight-average molecular weight (Mw) of the lactic acid polymer is (ii) about 19,000 to about 27,000, which is characterized in that area under the blood concentration-time curve (AUC) of an active ingredient for a period from one month to six months after the administration is 40% to 90% of the whole AUC, and has an excellent sustained-release profile;

(65) A pharmaceutical composition comprising the sustained-release composition according to the above-mentioned (1);

(66) A prophylactic or therapeutic agent for prostate cancer, prostatic hyperplasia, endometriosis, uterine fibroid, uterine fibroma, precocious puberty, dysmenorrhea, or breast cancer, or a contraceptive agent, comprising the sustained-release composition according to the above-mentioned (1);

(67) A prophylactic agent for premenopausal breast cancer postoperative recurrence, comprising the sustained-release composition according to the above-mentioned (1);

(68) A method for preventing or treating prostate cancer, prostatic hyperplasia, endometriosis, uterine fibroid, uterine fibroma, precocious puberty, dysmenorrhea, or breast cancer, or a method of contraception, comprising administering an effective amount of the sustained-release composition according to the above-mentioned (1) to a mammal;

(69) A method for preventing premenopausal breast cancer postoperative recurrence, comprising administering an effective amount of the sustained-release composition according to the above-mentioned (1) to a mammal;

(70) The method according to the above-mentioned (68) or (69), characterized in that the sustained-release composition is prepared by the method according to any one of the above-mentioned (42) to (54);

(71) Use of the sustained-release composition according to the above-mentioned (1) for the manufacture of a prophylactic or therapeutic agent for prostate cancer, prostatic hyperplasia, endometriosis, uterine fibroid, uterine fibroma, precocious puberty, dysmenorrhea or breast cancer, or a contraceptive agent;

(72) Use of the sustained-release composition according to the above-mentioned (1) for the manufacture of a prophylactic agent for premenopausal breast cancer postoperative recurrence; and the like.

BEST MODE FOR CARRYING OUT THE INVENTION

Figure 1:
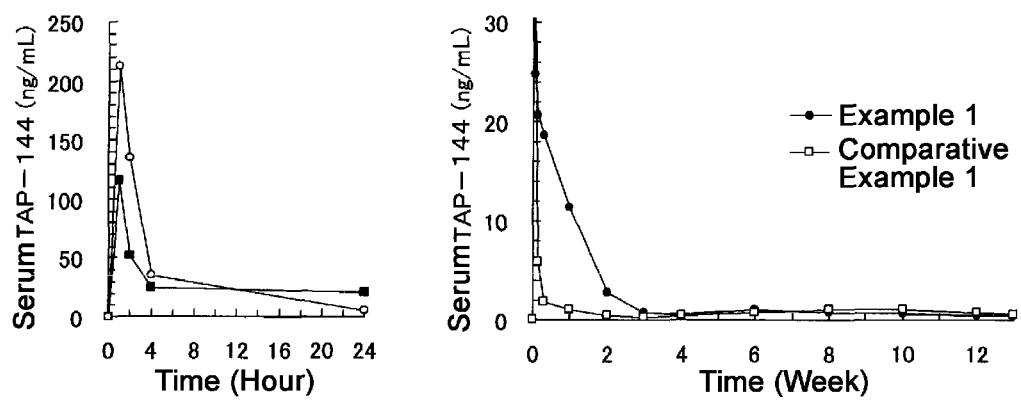
FIG. 1 is a graph showing each transition of blood drug level when the microcapsule powder prepared in Example 1 and Comparative Example 1 is respectively subcutaneously administered to a rat. The numerical value of the horizontal axis shows time, and the numerical value of the longitudinal axis shows a blood concentration.

While the water-soluble physiologically active peptide to be used in the present invention is not limited particularly as long as it is pharmacologically useful, for example, a physiologically active peptide having a molecular weight of about 300 to about 40,000, preferably, about 400 to about 30,000, more preferably, about 500 to about 20,000 is suitable.

The physiologically active peptide includes, for example, luteinizing hormone-releasing hormone (LH-RH), insulin, somatostatin, growth hormone, growth hormone releasing hormone (GH-RH), prolactin, erythropoietin, adrenal cortical hormone, melanocyte-stimulating hormone, thyroid-hormone releasing hormone, thyroid-stimulating hormone, luteinizing hormone, follicle-stimulating hormone, vasopressin, oxytocin, calcitonin, gastrin, secretin, pancreozymin, cholecystokinin, angiotensin, human placental lactogen, human chorionic gonadotropin, enkephalin, endorphin, kyotorphin, tuftsin, thymopoietin, thymosin, thymothymulin, thymic humoral factor, blood thymic factor, tumor necrosis factor, colony-inducing factor, motilin, dynorphin, bombesin, neurotensin, caerulein, bradykinin, atrial natriuretic factor, nerve growth factor, cell growth factor, neurotrophic factor, and peptides having an antagonistic action against endothelin, and derivatives thereof, and further includes the fragments thereof or the derivatives of the fragments and the like.

The physiologically active substance to be used in the present invention may be as it is, or a pharmaceutically acceptable salt thereof.

Examples of such a salt include, in the case that the physiologically active substance has a basic group such as an amino group, a salt with an inorganic acid (referred to also as an inorganic free acid) (e.g., carbonic acid, bicarbonic acid, hydrochloric acid, sulfuric acid, nitric acid, boric acid, etc.), an organic acid (referred to also as an organic free acid) (e.g., succinic acid, acetic acid, propionic acid, trifluoroacetic acid, etc.) or the like.

Examples of the salt include, in the case that the physiologically active substance has an acidic group such as a carboxyl group, a salt with an inorganic base (referred to also as an inorganic free base) (e.g., alkaline metal such as sodium and potassium, alkaline earth metal such as calcium and magnesium, etc.), an organic base (referred to also as an organic free base) (e.g., organic amines such as triethylamine, basic amino acids such as arginine, etc.) or the like. Moreover, the physiologically active peptide may form a metal complex compound (e.g., a copper complex, a zinc complex, etc.).

A preferred example of the physiologically active peptide includes an LH-RH derivative that is useful for a hormone dependent disease, especially, sex hormone dependent disease such as sex hormone dependent cancer (e.g., prostatic cancer, uterus cancer, breast cancer, hypophyseal tumor, etc.), benign prostatic hypertrophy, endometriosis, uterine fibroid, precocious puberty, dysmenorrhea, amenorrhea, premenstrual syndrome, multilocular ovarian syndrome and the like, and contraception (or infertility in the case of utilizing a rebound effect after the drug withdrawal) and premenopausal breast cancer postoperative recurrence, and a salt thereof. Furthermore, the example includes an LH-RH derivative that is effective for a benign or malignant tumor that is independent from sex hormone but susceptible to LH-RH, or the salt thereof.

A specific example of the LH-RH derivatives or the salt thereof includes, for example, Treatment with GnRH analogs: Controversies and perspectives [issued by The Parthenon Publishing Group Ltd., 1996] and a peptide described in JP-A 3-503165, JP-A 3-101695, JP-A 7-97334, JP-A 8-259460, and the like.

Examples of the LH-RH derivative include a LH-RH agonist or a LH-RH antagonist. As the LH-RH antagonist, for example, a physiologically active peptide represented by a general formula [I]:

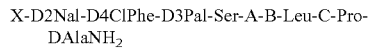

X-D2Nal-D4ClPhe-D3Pal-Ser-A-B-Leu-C-Pro-DAlaNH$_2$ wherein, X represents N(4H$_2$-furoyl)Gly or NAc, A represents a residue selected from NMeTyr, Tyr, Aph(Atz), and NMeAph(Atz), B represents a residue selected from DLys (Nic), DCit, DLys(AzaglyNic), DLys(AzaglyFur), DhArg (Et$_2$), DAph(Atz), and DhCi, and C represents Lys(Nisp), Arg, or hArg(Et$_2$), or a salt thereof is used.

As the LH-RH agonist, for example, a physiologically active peptide represented by a general formula [II]:

5-oxo-Pro-His-Trp-Ser-Tyr-Y-Leu-Arg-Pro-Z wherein, Y represents a residue selected from DLeu, DAla, DTrp, DSer(tBu), D2Nal and DHis(ImBzl), and Z represents NH—$C_2H_5$ or Gly-$NH_2$, or the salt thereof is used. In particular, a peptide in which Y is DLeu and Z is NH—$C_2H_5$ (that is, Peptide A represented by 5-oxo-Pro-His-Trp-Ser-Tyr-DLeu-Leu-Arg-Pro-NH—$C_2H_5$: leuprorelin) or a salt thereof (e.g., acetate) is suitable.

Those peptides can be prepared by a method described in the foregoing references or the publications or analogous methods thereof.

The abbreviations used herein represent the following:
Abbreviation: Name
N(4$H_2$-furoyl)Gly: N-tetrahydrofuroylglycine residue
NAc: N-acetyl group
D2Nal: D-3-(2-naphthyl)alanine residue
D4ClPhe: D-3-(4-chloro)phenylalanine residue
D3Pal: D-3-(3-pyridyl)alanine residue
NMeTyr: N-methyltyrosine residue
Aph(Atz): N-[5'-(3'-amino-1'H-1',2',4'-triazolyl)]phenylalanine residue
NMeAph(Atz): N-methyl-[5'-(3'-amino-1'H-1',2',4'-triazolyl)]phenylalanine residue
DLys(Nic): D-(e-N-nicotinoyl)lysine residue
Dcit: D-citrulline residue
DLys(AzaglyNic): D-(azaglycylnicotinoyl)lysine residue
DLys(AzaglyFur): D-(azaglycylfuranyl)lysine residue
DhArg($Et_2$): D-(N,N'-diethyl)homoarginine residue
DAph(Atz): D-N-[5'-(3'-amino-1'H-1',2',4'-triazolyl)]phenylalanine residue
DhCi: D-homocitrulline residue
Lys(Nisp): (e-N-isopropyl)lysine residue
hArg($Et_2$): (N,N'-diethyl)homoarginine residue Otherwise, an amino acid, when designated as an abbreviation, is based on an abbreviation by IUPAC-IUB Commission on Biochemical Nomenclature (European Journal of Biochemistry, Vol. 138, pages 9 to 37, 1984) or a common abbreviation in the art, and when an amino acid can have optical isomers, unless otherwise specified, it represents an L form.

The lactic acid polymer to be used in the present invention (hereinafter, occasionally abbreviated as lactic acid polymer of the present invention) includes a polymer consisting only of lactic acid, or a copolymer of lactic acid and other monomer (e.g., glycolic acid, etc.). The lactic acid polymer includes polylactic acid or polylactide. As the copolymer of lactic acid-glycolic acid, those having a composition ratio of lactic acid/glycolic acid of 60/40 to 99.9/0.1 can be used. In the sustained-release preparation of the present invention, polylactic acid or polylactide is preferred, especially, poly-DL-lactic acid or poly-DL-lactide is preferred.

Furthermore, the weight-average molecular weight of the lactic acid polymer used in the sustained-release preparation of the present invention is usually about 11,000 to about 27,000, preferably, about 11,600 to about 20,000 or about 19,000 to about 27,000. In particular, in the sustained-release preparation in which the release of the physiologically active substance in vivo from the preparation can maintain an effective drug blood concentration for a period from about 60 days to 130 days, about 11,600 to about 20,000 is preferable, about 12,000 to about 19,000 is more preferable, and about 13,000 to about 18,000 is further more preferable. On the other hand, in the sustained-release preparation in which the release of the physiologically active substance in vivo from the preparation can maintain an effective drug blood concentration for a period from about 120 days to 400 days, about 19,000 to about 27,000 is preferable, about 19,500 to about 26,500 is more preferable, and about 20,000 to about 26,000 is further more preferable.

When the weight-average molecular weight (Mw) of the lactic acid polymer is about 11,600 to about 20,000, it is preferable that a ratio of the weight-average molecular weight (Mw) to the number-average molecular weight (Mn) is more than 1.9. When the weight-average molecular weight (Mw) of the lactic acid polymer is about 19,000 to about 27,000, it is preferable that a ratio of the weight-average molecular weight (Mw) to the number-average molecular weight (Mn) is more than 1.5. Here, a weight-average molecular weight (Mw) and a number-average molecular weight (Mn) can be measured by a gel permeation chromatography (GPC).

In addition, the lactic acid polymer to be used in the sustained-release preparation in which the release of the physiologically active substance in vivo from the preparation can maintain an effective drug blood concentration for a period from about 120 days to 400 days is a polymer wherein, usually, a content of a polymer having a molecular weight of 5,000 or less is about 5% by weight or less, preferably, a content of a polymer having a molecular weight of 5,000 or less is about 5% by weight or less and a content of a polymer having a molecular weight of 3,000 or less is about 1.5% by weight or less, further preferably, a content of a polymer having a molecular weight of 5,000 or less is about 5% by weight or less, a content of a polymer having a molecular weight of 3,000 or less is about 1.5% by weight or less and a content of a polymer having a molecular weight of 1,000 or less is about 0.1% by weight or less.

A lactic acid polymer having a high-molecular weight to be a raw material of the lactic acid polymer of the present invention may be commercially available or those polymerized by a known method, and the weight-average molecular weight is usually about 11,000 to about 27,000, preferably, about 11,600 to about 20,000 or about 19,000 to about 27,000.

The known polymerization method includes, for example, a method of polycondensing lactic acid and glycolic acid if necessary, for example, a method by ring-opening polymerization of lactide, and if necessary, together with glycolide with using a catalyst such as Lewis acid such as diethyl zinc, triethyl aluminum and tin octylate, or metal salt, a method by ring-opening polymerization of lactide further in the presence of a hydroxycarboxylic acid derivative whose carboxyl group is protected, in the above-described method (e.g., International Publication WO 00/35990, and the like), in addition to a method by ring-opening polymerization wherein a catalyst is added to lactide under heating (e.g., J. Med. Chem, 16, 897 (1973)) and, for example, a method of copolymerizing lactide and glycolide.

Examples of the polymerization form include a bulk polymerization wherein lactide and the like is melted to be subjected to a polymerization, a solution polymerization wherein lactide and the like is dissolved in an appropriate solvent to be subjected to a polymerization. Among them, it is preferable in industrial production that a polymer obtained by a solution polymerization is used as a raw material of a lactic acid polymer of the present invention.

Examples of the solvent for dissolving lactide in the solution polymerization include aromatic hydrocarbons such as benzene, toluene and xylene, and dekalin, dimethylformamide and the like.

For hydrolyzing the lactic acid polymer having high-molecular weight obtained as described above, a hydrolysis method known per se is used, for example, the lactic acid polymer having a high-molecular weight may be dissolved in an appropriate solvent and then, react with adding water and if necessary, an acid.

Examples of the solvent for dissolving the lactic acid polymer having a high-molecular weight include a solvent that can dissolve the lactic acid polymer with an amount of 10-fold weight or less of the polymer, and specifically include a halogenated hydrocarbons such as chloroform and dichloromethane, aromatic hydrocarbons such as toluene, o-xylene, m-xylene and p-xylene, and cyclic ethers such as tetrahydrofuran, acetone, N,N-dimethylformamide and the like. Additionally, in the polymerization of a lactic acid polymer having a high-molecular weight, when a solvent available for hydrolysis of a lactic acid polymer having a high-molecular weight is used, operations of the polymerization and the hydrolysis can be performed continuously without isolation of the polymerized lactic acid polymer having a high-molecular weight.

The amount of the solvent to be used for dissolving the lactic acid polymer having a high-molecular weight is generally 0.1 to 100 times, preferably 1 to 10 times to the lactic acid polymer as a solute.

The additive amount of water is generally 0.001 to 1-fold weight, preferably 0.01 to 0.1-fold weight to the lactic acid polymer having a high-molecular weight.

The acid to be added if necessary, includes an inorganic acid such as hydrochloric acid, sulfuric acid, and nitric acid, and an organic acid such as lactic acid, acetic acid, trifluoroacetic acid, and preferably a lactic acid.

The additive amount of the acid is generally 0 to 10-fold weight, and preferably 0.1 to 1-fold weight to the lactic acid polymer having a high-molecular weight.

The temperature of the hydrolysis reaction is generally 0 to 150° C., preferably 20 to 80° C.

The time of the hydrolysis reaction may vary depending on the weight-average molecular weight of the lactic acid polymer having a high-molecular weight and the reaction temperature, and is generally 10 minutes to 100 hours, and preferably 1 to 20 hours.

The termination time of the hydrolysis treatment is determined based on the weight-average molecular weight of the hydrolysis product. That is, sampling is appropriately performed during the hydrolysis treatment, the weight-average molecular weight of the hydrolysis product in the sample is measured by a gel permeation chromatography (GPC) and, if it is confirmed that the molecular weight is in the targeted numeric range, the hydrolysis treatment is terminated.

As a method for precipitating the targeted lactic acid polymer from the solution containing the hydrolysis product obtained by subjecting the lactic acid polymer having a high-molecular weight to hydrolysis as described above, a method contacting the solution containing the hydrolysis product with a solvent that can precipitate the targeted lactic acid polymer contained therein, and the like are exemplified.

Examples of a preferable embodiment of the solution containing hydrolysis product include, for example, a solution in which about 10 to 50 wt % of the lactic acid polymer having a weight-average molecular weight of 15,000 to 50,000, preferably 15,000 to 30,000, more preferably 17,000 to 26,000, especially preferably 17,500 to 25,500 is dissolved in a solvent capable of dissolving the lactic acid polymer having a high-molecular weight such as halogenated hydrocarbons such as chloroform and dichloromethane, aromatic hydrocarbons such as toluene, o-xylene, m-xylene, and p-xylene, and cyclic ethers such as tetrahydrofuran, acetone, N,N-dimethylformamide. When the sustained-release preparation of the present invention does not contain hydroxynaphthoic acid, a solution in which about 10 to 50 wt % of the lactic acid polymer having a weight-average molecular weight of 15,000 to 50,000, preferably 15,000 to 40,000 is dissolved, and the like are exemplified.

Examples of the solvent capable of precipitating the targeted lactic acid polymer contained in the solution containing hydrolysis product include, for example, alcohols such as methanol and ethanol, chain-ethers such as isopropyl ether, aliphatic hydrocarbons such as hexane, water and the like.

The amount to be used of the solvent capable of precipitating the targeted lactic acid polymer is generally 0.1 to 100-fold weight, preferably, 1 to 10-fold weight to the solvent in the solution containing hydrolysis product.

The preferable specific example of the combination of kind and amount to be used of such solvent includes an embodiment wherein isopropyl ether as a solvent for reducing the solubility is used with an amount of 2 to 10-fold weight to the dichloromethane in terms of the solution containing hydrolysis product wherein 1 to 5-fold weight of dichloromethane is used as a solvent to the solute.

When the solvent capable of precipitating the targeted lactic acid polymer as a solute is contacted with the solution containing hydrolysis product, the temperature of the solvent is generally −20 to 60° C., preferably, 0 to 40° C., and the temperature of the solution containing hydrolysis product is generally 0 to 40° C., preferably 10 to 30° C.

Examples of the method for contacting the solvent and the solution containing hydrolysis product include a method of adding the solution containing hydrolysis product into the solvent at one time, a method of adding dropwise the solution containing hydrolysis product to the solvent, a method of adding the solvent to the solution containing hydrolysis product at one time, or a method of adding dropwise the solvent to the solution containing hydrolysis product.

The lactic acid polymer of the present invention obtained as described above is preferable as a base substrate for a sustained-release preparation because the amount of terminal carboxyl groups is in a preferable range as a base substrate for a sustained-release preparation.

In the sustained-release preparation of the present invention, a fatty acid can be added into the microcapsule of the sustained-release preparation so that the blood drug concentration is idealized in an onset part within a certain period from the early stage on the administration to a patient and a water-soluble physiologically active peptide as an active ingredient can be stably sustained-released over a more longer period of time.

The fatty acid to be used in the present invention means a carboxylic acid that has a chain structure of straight chain or alkyl group having side chain and has one carboxyl group, as well as benzoic acid, hydroxynaphthoic acid, and pamoic acid. The carboxylic acid that has a chain structure of straight chain or alkyl group having side chain is preferably those having four or more carbons, and specifically includes butyric acid, valeric acid, caproic acid, enanthic acid, caprylic acid, pelargonic acid, capric acid, undecylic acid, lauric acid, tridecylic acid, myristic acid, pentadecylic acid, palmitic acid, heptadecylic acid, stearic acid, nonadecanoic acid, arachidic acid, isocrotonic acid, undecylenic acid, oleic acid, elaidic acid, sorbic acid, linoleic acid, lionlenic acid, arachidonic acid, and the like. Stearic acid, benzoic acid, hydroxynaphthoic acid, pamoic acid and the like are more preferred.

While the additive amount of the fatty acid may vary depending on the kind of fatty acid, the kind of water-soluble physiological active peptide and additive amount thereof, the period of sustained release, and the like, it is 0.1 to 10 moles, preferably 0.2 to 5 moles, further more preferably 0.25 to 2 moles, especially preferably 0.5 to 1.5 moles, to 1 mole of the water-soluble physiologically active peptide or a salt thereof.

Moreover, the weight ratio of the fatty acid to the whole microcapsule is about 0.01 to about 50% by weight, preferably about 0.1 to about 25% by weight, further more preferably about 2 to 10% by weight.

While the weight ratio of the water-soluble physiologically active peptide in the composition of the present invention may vary depending on the kind of the physiologically active peptide, the desired pharmacological effect, duration of the effect, and the like, it is about 15 to about 35% by weight, preferably, about 16 to about 30% by weight, more preferably about 17 to about 26% by weight, further more preferably about 17 to about 23% by weight, and most preferably about 18 to about 22% by weight to the whole microcapsule (the content of the physiologically active substance in the microcapsule).

While the weight ratio of the physiologically active substance in the composition of the present invention may vary depending on the kind of physiologically active substance, the desired pharmacological effect, duration of the effect, and the like, it is, in the sustained-release composition containing the physiologically active substance or a salt thereof and the lactic acid polymer or a salt thereof, about 0.001 to about 50% by weight, preferably about 0.02 to about 40% by weight, more preferably about 0.1 to about 30% by weight, and most preferably about 14 to about 24% by weight relative to the sum of the composition, and in the case of non-peptidic physiologically active substance or the salt thereof, the weight ratio is about 0.01 to about 80% by weight, and preferably about 0.1 to about 50% by weight.

The form of the sustained-release composition herein is, but not limited to, preferably a form of fine particles, especially preferably a form of microsphere (referred to also as a microcapsule in the case of the sustained-release composition containing the lactic acid polymer). Moreover, the microsphere herein indicates an injectable spherical fine particle that can be dispersed in a solution. The form can be confirmed through observation by, for example, a scanning electron microscope.

A method for producing the sustained-release composition (for example, a microcapsule) containing the present physiologically active substance or a salt thereof and the present lactic acid polymer or a salt thereof will be exemplified below.

In the following production process, where appropriate, a drug retaining agent (e.g., gelatin, salicylic acid and the like) may be added by a method known per se.

In the present method, firstly, the lactic acid polymer of the present invention (hereinafter, referred to also as a biodegradable polymer of the present invention) or a salt thereof is dissolved in a volatile water-immiscible first solvent to prepare a first solution. The solvent used as the above-described first solvent has preferably a boiling point of 100° C. or lower.

As the first solvent, for example, a halogenated hydrocarbon (e.g., dichloromethane, chloroform, dichloroethane, trichloroethane, carbon tetrachloride, and the like), ethers (e.g., diethyl ether, diisopropyl ether, and the like), a fatty ester (e.g., ethyl acetate, butyl acetate, and the like), an aromatic hydrocarbon (e.g., benzene, toluene, xylene, and the like) are used. Among them, a halogenated hydrocarbon is preferable, and dichloromethane is especially suitable. Moreover, they may be mixed to use at an appropriate ratio.

The concentration of the biodegradable polymer of the present invention in an organic solvent solution may vary depending on the molecular weight of the biodegradable polymer of the present invention and the kind of the organic solvent, but, for example, when dichloromethane is used as an organic solvent, the concentration is generally selected from about 0.5 to about 70% by weight, more preferably about 1 to about 60% by weight, and especially preferably about 33 to about 45% by weight.

Then, the physiologically active substance comprised of the water-soluble physiologically active peptide is dissolved in a water-miscible second solvent to prepare a second solution. The water-miscible solvent used as the above second solvent is miscible with water at a constant rate, and preferably has a boiling point of 100° C. or lower.

As the second solvent, for example, lower alcohols (e.g., methanol, ethanol, propanol, and the like), acetonitrile, acetone, tetrahydrofuran and the like are used. Among them, a lower alcohol is preferable, and methanol and ethanol are especially suitable. In addition, they may be mixed to use at an appropriate ratio.

Furthermore, as a solvent to dissolve the lactic acid polymer or a salt thereof in preparing the first solution, in addition to the use of the first solvent, a water-miscible third solvent can be added thereto. In this case, the third solvent can be selected from the same solvent as the second solvent.

Subsequently, the resultant first solution and the second solution are mixed to prepare a third solution. The resultant third solution is preferably a solution wherein the lactic acid polymer or a salt thereof and the physiologically active substance are uniformly dissolved, and additionally, in the next step, the lactic acid polymer or a salt thereof and the physiologically active substance are not deposited during the process of removing the solvent from the solution.

In this case, the physiologically active substance is to be added so that the physiologically active substance is contained with the amount of 15 to 35 (weight/weight) % to the whole microcapsule (content of the physiologically active substance in microcapsule). Therefore, the loading amount of drug such as physiologically active substance is about 17 to about 50% by weight, preferably about 18 to about 43% by weight, more preferably about 19 to about 38% by weight, further more preferably about 19 to about 25% by weight, and most preferably about 20 to about 23% by weight. Herein, the loading amount is a calculated rate of the added amount of physiologically active substance to the total additive amount of each component comprising the microcapsule in the preparation. On the other hand, the entrapment ratio of the drug such as physiologically active substance is about 75% by weight or more, preferably about 80% by weight or more, more preferably about 82% by weight or more, further more preferably about 85% by weight or more, and most preferably about 89% by weight or more. Herein, the entrapment ratio is a calculated rate of the drug incorporated into microcapsule to the added amount of the physiologically active substance.

The volume ratio of the above water-immiscibile solvent and water-miscible solvent (including the third solvent in the case that the third solvent is added to the first solvent) to be used in the step preparing the third solution is generally 35:65 to 55:45.

Then, the resultant third solution is dispersed into a fourth solution comprised of aqueous solution of an emulsifier to prepare the O (oil phase)/W (water phase) emulsion, and then microcapsule is prepared by removing the above-mentioned first and second solvents. When a third solvent is added to the first solvent, the third solvent is simultaneously removed at this step. In this case, the water phase volume is generally selected from about 1 to about 10,000 times, more preferably about 5 to about 5,000 times, and especially preferably about 10 to about 2,000 times of the oil phase volume.

The emulsifier contained in the above water phase generally may be any emulsifier which can form a stable O/W emulsion. Specifically, for example, anionic surfactants (e.g., sodium oleate, sodium stearate, sodium lauryl sulfate, and the like), nonionic surfactants (e.g., polyoxyethylene sorbitan fatty ester [Tween 80, Tween 60; Atlas Powder Co. Ltd], polyoxyethylene castor oil derivatives [HCO-60, HCO-50, Nikko Chemicals Co. Ltd], and the like), polyvinylpyrrolidone, polyvinyl alcohol, carboxymethylcellulose, lecithin, gelatin, and hyaluronic acid are used. One kind or some of these may be used alone or in combination. The concentration upon use is preferably in the range of about 0.01 to 10% by weight, and more preferably in the range of about 0.05 to about 5% by weight.

An osmo-regulator may be added to the above water phase. Said osmo-regulator may be any one which shows an osmotic pressure in aqueous solution.

Examples of the osmo-regulators include, for example, polyvalent alcohols, monovalent alcohols, monosaccharides, disaccharides, oligosaccharide and amino acids or derivatives thereof.

For the above polyvalent alcohols, for example, trivalent alcohols such as glycerin, pentavalent alcohols such as arabitol, xylitol, and adonitol, hexavalent alcohols such as mannitol, sorbitol and dulcitol are used. Among them, hexavalent alcohols is preferable, and mannitol is especially suitable.

The above monovalent alcohols include, for example, methanol, ethanol, and isopropyl alcohol, and among them, ethanol is preferable.

For the above monosaccharides, for example, pentoses such as arabinose, xylose, ribose and 2-deoxyribose, hexoses such as glucose, fructose, galactose, mannose, sorbose, rhamnose and fucose are used, and among them, hexoses are preferable.

For the above oligosaccharide, for example, trisaccharide such as maltotriose and raffinose, tetrasaccharide such as stachyose are used, and among them, trisaccharide is preferable.

As the derivatives of the monosaccharide, disaccharides and oligosaccharide mentioned above, for example, glucosamine, galactosamine, glucuronic acid, galacturonic acid and the like are used.

As the above amino acids, any one can be used as long as it is L-form. For example, glycine, leucine, arginine and the like are exemplified. Among them, L-arginine is preferable.

These osmo-regulators may be used alone or with a mixture.

These osmo-regulators are used at a concentration that makes the osmotic pressure of outer water phase about 1/50 to about 5 times, preferably about 1/25 to about 3 times of the osmotic pressure of a physiological saline. When mannitol is used as the osmo-regulator, the concentration is preferably 0.5 to 1.5%.

As the method for removing the first and second solvents (including a third solvent, when third solvent is added to the first solvent; the same is applied hereinafter), a method known per se or analogous method thereto is used. The examples of the method include a method for evaporating an organic solvent under ambient pressure or with gradually reducing pressure with stirring by a propeller type stirrer, magnetic stirrer or the like, and a method for evaporating an organic solvent with regulating vacuum using rotary evaporator, and the like. Especially, an in-water drying method wherein the solvent is removed with stirring under ambient pressure is preferable.

In the sustained-release preparation of the present invention, the control temperature of the emulsification process in which the first and second solvents are removed may be adjusted in order to idealize the blood drug concentration of a maintenance part in one month or later after the administration to patients, and stably and sustainably release the water-soluble physiologically active peptide as an active ingredient.

The control temperature of the emulsification process in which the first and second solvents are removed can be adjusted to, for example, about 5 to 50° C. Further, it is preferably adjusted to about 15 to 35° C., especially about 15 to 30° C. In this case, the method for controlling temperature includes a method of adjusting the above O/W emulsion to the above temperature, and a method of preparing an emulsion by mixing the third and fourth solutions adjusted to the above temperature, as well as a method of placing all processes of the emulsification process in an environment set at the control temperature.

The microcapsule thus obtained is collected by centrifugation or filtration, and then washed repeatedly with distilled water several times to remove the free physiologically active substance, emulsifier and the like which are adhered to the surface of microcapsule, and then the microcapsule is re-dispersed into distilled water before lyophilized.

During the preparation process, an agglutination inhibitor may be added to prevent agglutination of the particles. The agglutination inhibitor includes, for example, a water-soluble polysaccharide such as mannitol, lactose, glucose, and starches (e.g., corn starch), amino acids such as glycine, and proteins such as fibrin and collagen. Among them, mannitol is suitable.

The additive amount of the agglutination inhibitor such as mannitol is generally 0 to about 24% by weight to the whole microcapsule.

In addition, after lyophilization, where necessary, the microcapsules may be heated under reduced pressure and the condition of not causing a mutual fusion of microcapsules, to remove water and the organic solvents in microcapsules. It is preferable to heat at a temperature around or slightly higher than the intermediate point glass transition temperature of biodegradable polymer determined by a differential scanning calorimeter under the conditions of temperature increasing speed of 10 to 20° C. per minute. It is more preferable to heat at a temperature around the intermediate point glass transition temperature of biodegradable polymer or within the range of temperature higher by about 30° C. than the intermediate point glass transition temperature. Especially, when a lactic acid-glycolic acid polymer is used as a biodegradable polymer, heating is conducted preferably at temperatures lying within the range from around the intermediate point glass transition temperature to a temperature higher than the intermediate point glass transition temperature by 10° C., further preferably at temperatures lying within the range from around the intermediate point glass transition temperature to a temperature higher than the intermediate point glass transition temperature by 5° C.

Although the heating time may vary depending on the amount of microcapsules and the like, it is generally about 12 hours to 168 hours, preferably about 24 hours to 120 hours, especially preferably about 48 hours to 96 hours after the microcapsule itself reached the predetermined temperature.

The heating method is not especially limited as long as a set of microcapsules can be uniformly heated.

As the heat-drying method, for example, a method of heat-drying in thermostat bath, fluidized bath, moving bath or kiln, and a method of heat-drying by microwave. Among them, the method of heat-drying in thermostat bath is preferable.

In the production of the sustained-release preparation containing a fatty acid of the present invention, it can be prepared by adding a fatty acid to the first solution that is a polymer solution and/or the second solution that is a physiologically active peptide solution or the third solution that is a mixed solution thereof.

A method for preparing the sustained-release preparation containing a fatty acid of the present invention is exemplified below.

In the method, first, the lactic acid polymer of the present invention or a salt thereof is dissolved in a volatile and water-immiscible first solvent to prepare a first solution. In the solvent used as the above first solvent, preferably the boiling point is 100° C. or lower.

The first solvent includes, for example, halogenated hydrocarbons (e.g., dichloromethane, chloroform, dichloroethane, trichloroethane, carbon tetrachloride, and the like), ethers (e.g., ethyl ether, isopropyl ether, and the like), fatty esters (e.g., ethyl acetate, butyl acetate, and the like), aromatic hydrocarbons (e.g., benzene, toluene, xylene, and the like). Among them, halogenated hydrocarbons are preferable, and especially dichloromethane is suitable. They may be mixed to use at an appropriate ratio.

The concentration of the biodegradable polymer of the present invention in the organic solvent solution may vary depending on the molecular weight of the biodegradable polymer of the present invention and the kind of organic solvent, and for example, when dichloromethane is used as an organic solvent, the concentration is selected generally from about 0.5 to about 70% by weight, more preferably about 1 to about 60% by weight, especially preferably about 33 to about 45% by weight.

When the fatty acid is added to the first solution that is a polymer solution, the fatty acid is added to the first solvent after the biodegradable polymer is dissolved into the first solvent or when the biodegradable polymer is dissolved into the first solvent. At this time, if the fatty acid is dissolved when the third solution described below is prepared, the fatty acid does not need to be completely dissolved at this step, but a solubilizing agent can be used to dissolve the fatty acid as appropriate. The solubilizing agent is not especially limited as long as it can be used as the first solvent or as the second solvent that is a solvent for a physiologically active peptide, and lower alcohols to be used as the second solvent are preferred, and methanol and ethanol are particularly preferred. In addition, it may be heated to dissolve the fatty acid.

Then, the physiologically active substance comprised of a water-soluble physiologically active peptide is dissolved in a water-miscible second solvent to prepare a second solution. The solvent used as above second solvent is miscible with water at a constant rate, and the boiling point is preferably 100° C. or lower.

As the second solvent, for example, lower alcohols (e.g., methanol, ethanol, propanol, and the like), acetonitrile, acetone, tetrahydrofuran, and the like are used. Among them, lower alcohols are preferable, and especially methanol or ethanol is suitable. Further, they may be mixed to use at an appropriate ratio.

In addition, as a solvent for dissolving the lactic acid polymer or a salt thereof in the preparation of the first solution, in addition to the use of the first solvent, further a water-miscible third solvent can be added thereto. In this case, the third solvent may be selected from the same solvents as the second solvents.

When the fatty acid is added to the second solution which is a solution of physiologically active peptide, the fatty acid is added to the second solvent after the physiologically active peptide is dissolved in the second solvent or when the physiologically active peptide is dissolved in the second solvent. At this time, if the fatty acid is dissolved when the third solution described below is prepared, the fatty acid does not need to be completely dissolved at this step, but a solubilizing agent can be used to dissolve the fatty acid as appropriate. The solubilizing agent is not limited as long as it can be used as the first solvent or as the second solvent. In addition, it may be heated to dissolve the fatty acid.

Subsequently, the obtained first and second solutions are mixed to prepare the third solution. It is desirable that the third solution obtained here a solution wherein the lactic acid polymer or a salt thereof and the physiologically active substances are uniformly dissolved, and additionally, in the next step, the lactic acid polymer or a salt thereof and the physiologically active substance are not deposited during the process of removing the solvent from the solution. Further, when a fatty acid is added, it is desirable that the fatty acid is uniformly dissolved, and further in the next step, it is not precipitated.

In this case, the physiologically active substance is to be added so that the physiologically active substance is contained with the amount of 15 to 35 (weight/weight) % to the whole microcapsule (a content of the physiologically active substance in microcapsule). Therefore, the loading amount of drug as a physiologically active substance is about 17 to about 50% by weight, preferably about 18 to about 43% by weight, more preferably about 19 to about 38% by weight, further more preferably about 19 to about 25% by weight, most preferably about 20 to about 22% by weight. A loading amount is a calculated rate of the added amount of the physiologically active substance to the total additive amount of each component comprising microcapsule in the preparation. The entrapment ratio of drug such as physiologically active substance is about 75% by weight or more, preferably about 80% by weight or more, more preferably about 82% by weight or more, further more preferably about 85% by weight or more, most preferably about 89% by weight or more. Herein, the entrapment ratio is a calculated rate of the drug incorporated into microcapsule to the additive amount of the physiologically active substance.

The volume ratio of the above water-immiscible solvent and water-miscible solvent (including the third solvent when the third solvent is added to the first solvent) to be used in the step of preparing the third solution is generally 35:65 to 55:45.

When a fatty acid is added to the third solution which is a solution of physiologically active peptide, the fatty acid is added to the third solution when the first and second solutions are mixed or after the first and second solutions are mixed. At this time, a solubilizing agent can be used to dissolve the fatty acid as appropriate. The solubilizing agent is not limited as long as it can be used as the first solvent or as the second solvent, and lower alcohols used as the second solvent are preferred, and methanol and ethanol are particularly preferred. In addition, the solvent may be heated to dissolve the fatty acid.

As mentioned above, the fatty acid can be added at any step in the process for preparing the first solution and/or the second solution or for preparing the third solution that is a mixed solution thereof. The timing of the addition of the fatty acid is not limited as long as the fatty acid is dissolved in an oil phase at the time when the third solution is emulsified into the fourth solution to form an emulsion, and it is determined depending on the kind of the fatty acid and the kind of the solvent used in each step because the solvent to dissolve may vary depending on the kind of the fatty acid. The fatty acid is preferably added to a solvent having a high-solubility of the fatty acid used because if the fatty acid is added to a solvent having a low-solubility, a solubilizing agent may be needed, and there is a possibility that a ratio of the first and second solvents is influenced. When a stearic acid is used as fatty acid, it is preferable to add to the second solvent and heat to dissolve together the physiologically active peptide.

Then, the resultant third solution is dispersed into a fourth solution comprised of an aqueous solution of an emulsifier to prepare the O (oil phase)/W (water phase) emulsion, and microcapsule is prepared by removing the above-mentioned first solvent and second solvent. When a third solvent is added to the first solvent or a solubilizing agent is used to dissolve the fatty acid, the third solvent or the solubilizing agent is simultaneously removed at this step. In this step, the water phase volume is generally selected from about 1 to about 10,000 times, more preferably about 5 to about 5,000 times, especially preferably about 10 to about 2,000 times of an oil phase volume.

For the emulsifier contained in the above water phase, the same emulsifier as those exemplified in the above sustained-release preparation not containing the fatty acid can be used.

In addition, an osmo-regulator may be added to the above water phase. The osmo-regulator may be any osmo-regulator which shows an osmotic pressure in the water solution thereof, and the same osmo-regulator as those exemplified in the above sustained-release preparation not containing the fatty acid can be used.

As a method for removing the first and second solvent (including a third solvent or a solubilizing agent, when third solvent is added to the first solvent or solubilizing agent is used to dissolve the fatty acid; the same is applied hereinafter), a method known per se or an analogous method thereto is used. For example, an example of the method includes a method of evaporating organic solvent under ambient pressure or with gradually reducing pressure as stirring using a propeller type stirrer or a magnetic stirrer, or a method of evaporating organic solvent by regulating vacuum degree with rotary evaporator. In particular, an in-water drying method wherein a solvent is removed with stirring under ambient pressure is preferable.

The control temperature of the emulsification process in which the first and second solvents are removed can be adjusted to, for example, about 5 to 50° C. Further, it is preferable to adjust to about 15 to 35° C. In this case, a method for controlling temperature includes a method of adjusting the above O/W emulsion to the above temperature, and a method of preparing an emulsion by mixing the third and fourth solutions adjusted to the above temperature, as well as a method of placing all processes of the emulsification process in an environment set at the control temperature.

The microcapsule thus obtained is collected by centrifugation or filtration, and then washed repeatedly with distilled water several times to remove the free physiologically active substance, emulsifier and the like which is adhered to the surface of the microcapsule, and then the microcapsule is re-dispersed into distilled water before lyophilized.

During the preparation process, an agglutination inhibitor may be added to prevent agglutination of the particles. The agglutination inhibitor includes, for example, a water-soluble polysaccharides such as mannitol, lactose, glucose, and starches (e.g., corn starch), amino acids such as glycine, and proteins such as fibrin and collagen. Among them, mannitol is suitable.

The additive amount of the agglutination inhibitor such as mannitol is generally 0 to about 24% by weight to the whole microcapsule.

In addition, after lyophilization, where appropriate, the microcapsules may be heated under reduced pressure and the condition of not causing a mutual fusion of microcapsules, to remove water and the organic solvents in microcapsules. It is preferable to heating at a temperature around or slightly higher than the intermediate point glass transition temperature of biodegradable polymer determined by a differential scanning calorimeter under the condition of temperature increasing speed of 10 to 20° C. per minute. It is more preferable to heat at a temperature around the intermediate point glass transition temperature of biodegradable polymer or within the range of temperature higher by about 30° C. than the intermediate point glass transition temperature. Especially, when a lactic acid-glycolic acid polymer is used as a biodegradable polymer, heating is conducted preferably at temperatures lying within the range from around the intermediate point glass transition temperature to a temperature higher than the intermediate point glass transition temperature by 10° C., further more preferably at temperatures lying within the range from around the intermediate point glass transition temperature to a temperature higher than the intermediate point glass transition temperature by 5° C.

Although the heating time may vary depending on the amount of microcapsule, it is generally about 12 hours to 168 hours, preferably about 24 hours to 120 hours, especially preferably about 48 hours to 96 hours after the microcapsule itself reached the predetermined temperature.

The heating method is not especially limited as long as a set of microcapsules can be uniformly heated.

As the heat-drying method, for example, a method of heat-drying in thermostat bath, fluidized bath, moving bath, or kiln, and a method of heat-drying by microwave. Among them, the method of heat-drying in thermostat bath is preferable.

The sustained-release preparation of the present invention obtained by the above preparation methods can be obtained as a preparation in which a physiologically active substance comprised of a water-soluble physiologically active peptide is substantially uniformly dispersed in a microcapsule comprised of a lactic acid polymer or a salt thereof. Herein, the "substantially uniformly dispersed" means that a water-soluble physiologically active peptide is substantially uniformly dispersed in the biodegradable polymer. For example, it includes, but not limited to, a microcapsule hardened by removing organic solvent using in-water drying method from a microcapsule generated by subjecting to an emulsification process with the state that the physiologically active peptide and the biodegradable polymer are fully dissolved in the organic solvent. Thereby, the suppression of initial excessive release of the physiologically active peptide after administration and a stable drug release in onset part can be achieved, additionally a sustained-release of a physiologically active substance can also be achieved at drug levels in the effective blood concentration for a period from about 60 to 400 days after the administration.

As the sustained-release preparation of the present invention obtained by the above preparing method contains 15 to 35 (weight/weight) % of a water-soluble physiologically active peptide per unit weight of the preparation, the content of the physiologically active substance in the preparation is higher contained than the conventional preparation. As the result, the rate of content of the physiologically active peptide per unit volume of a microcapsule can be elevated to 15 to 35 (weight/weight) %, the volume or weight of the whole sustained-release preparation needed per unit dose of an effective ingredient can be reduced. Thereby, a physical burden of patients such as pain at administration and induration after administration which is considered as the result of the administration of a preparation having large unit volume can be reduced.

The sustained-release composition of the present invention may be in from of microsphere, microcapsule, and microparticle, and microcapsule is suitable.

The sustained release composition of the present invention can be administered as itself or formulated as a starting material into any of various dosage forms such as an intramuscular, subcutaneous or organ injection or implantation formulation, a nasal, rectal and intrauterine mucosal formulation, an oral formulation (e.g., a solid dosage form such as capsule (e.g., hard capsule and soft capsule, and the like), granule and powder, or a liquid formulation such as a syrup, an emulsion, a suspension, and the like) and the like.

For example, when the sustained-release composition of the present invention is formulated into an injection formulation, it can be formulated into an aqueous suspension together with a dispersing agent (e.g., surfactant such as Tween 80 and HCO-60, polysaccharide such as sodium hyaluronate, carboxymethyl cellulose, sodium arginate, and the like), a preservative (e.g., methylparaben, propylparaben, and the like), an isotonic agent (e.g., sodium chloride, mannitol, sorbitol, glucose, proline, and the like), or into an oil suspension by dispersing together with a vegetable, oil such as sesame oil and corn oil to obtain a practically utilizable sustained release injection formulation.

When the sustained-release preparation of the present invention is dispersed into a dispersion medium then administered as an aqueous suspension, it has excellent easy dispersibility against the dispersion medium and is stable for a period of 24 hours or more after dispersing. Thereby, an operativity related with preparing at administration on medical site can be better.

A particulate diameter of the sustained-release composition of the present invention, when used as a suspending injection formulation, is any diameter within range satisfying the dispersibility and needle permeability, for example, a mean particulate diameter is about 0.1 to 300 μm, preferably about 0.5 to 150 μm, more preferably about 1 to 100 μm.

A method of making the sustained-release composition of the present invention to a sterile preparation includes, but not limited to, a method of making all preparing process to be sterile, a method of sterilizing by gamma-ray, and a method of adding an antiseptic agent.

The sustained-release composition of the present invention is low toxicity, thus it can be used in a mammal (e.g., human, cattle, pig, dog, cat, mouse, rat, and rabbit, ant the like) as a safe medicine.

While a dose of the sustained-release composition of the present invention may vary depending on the type and content of a physiologically active substance as a main ingredient, the dosage form, the duration of the release of a physiologically active substance, the target disease, and the target animal, it may be an effective amount of the physiologically active substance. A single dose of the physiologically active substance as a main ingredient, for example when the sustained release preparation is a 6-month preparation, can be appropriately selected from preferably about 0.01 to 10 mg/kg weight per an adult, more preferably about 0.05 to 5 mg/kg weight per an adult.

The single dose of the sustained-release composition can be appropriately selected from preferably a range from about 0.05 to 50 mg/kg weight pre an adult, more preferably a range from about 0.1 to 30 mg/kg weight pre an adult.

A frequency of administration can be appropriately selected depending on the type and content of a physiologically active substance as a main ingredient, the dosage form, the duration of the release of a physiologically active substance, the target disease, and the target animal, such as once per several weeks, once a month, once per several months (e.g., 3, 4, or 6 months, and the like).

The sustained-release preparation of the present invention can suppress an excessive release of the water-soluble physiologically active peptide within 1 day after the administration, and stabilize the blood drug concentration in patient body over the long-term by the stable release of the drug in an onset part for a period from 1 day to about 1 month after the administration. As a result, the release of the physiologically active substance can be maintained at the effective blood drug concentration for a period from about 60 to 400 days after the administration.

That is, when the sustained-release preparation of the present invention is administered, for example applying to an experimental animal such as rat and the like, the ratio of a maximum blood concentration of the active ingredients within 24 hours after the administration to the average blood concentration of the active ingredients from 24 hours to 1 month after the administration is 2 to 90, and the ratio of the maximum blood concentration of active ingredients within 24 hours after the administration to the average blood concentration of the active ingredients from 1 month after the administration to the sustained-release period the preparation predetermines is 20 to 500. Area under the blood concentration-time curve (AUC) of the active ingredient within 24 hours after the administration calculated from the blood concentration is 1 to 30% of the total AUC, and AUC of the active ingredient from 24 hours to 1 month after the administration calculated from the blood concentration is 10 to 80% of the total AUC, and AUC of the active ingredient from 1 month after the administration to the sustained-release period the preparation predetermines is 10 to 90% of the total AUC.

In particular, when the sustained-release preparation of the present invention using a lactic acid polymer which the weight-average molecular weight (Mw) is about 11,600 to about 20,000 is administered to a patient, the release of the physiologically active substance from the sustained-release composition in vivo can be maintained at the effective blood drug concentration for a period from about 60 to 130 days. In this case, for example, as applying to an experimental animal such as rat and the like, the ratio of the maximum blood concentration of the active ingredients within 24 hours after the administration to the average blood concentration of the active ingredients from 24 hours to 1 month after the administration is 2 to 50, and the ratio of the maximum blood concentration of the active ingredients within 24 hours after the administration to the average blood concentration of the active ingredients from 1 month to 3 months after the administration is 20 to 350. AUC of the active ingredient within 24 hours after the administration calculated from the blood concentration is 3 to 30% of the total AUC, and AUC of the active ingredient from 24 hours to 1 month after the administration calculated from the blood concentration is 40 to 80% of the total AUC, and AUC of the active ingredient from 1 month to 3 months after the administration is 10 to 35% of the total AUC.

When the sustained-release preparation of the present invention using a lactic acid polymer which the weight-average molecular weight (Mw) is about 19,000 to about 27,000 is administered to a patient, the release of the physiologically active substance from the sustained-release composition in vivo can be maintained at the effective blood drug concentration for a period from about 120 to 400 days. In this case, for example, as applying to an experimental animal such as rat and the like, the ratio of the maximum blood concentration of the active ingredients within 24 hours after the administration to the average blood concentration of the active ingredients from 24 hours to 1 month after the administration is 10 to 90, and the ratio of the maximum blood concentration of the active ingredients within 24 hours after the administration to the average blood concentration of the active ingredients from 1 month to 6 months after the administration is 20 to 500. AUC of the active ingredient within 24 hours after the administration calculated from the blood concentration is 1 to 20% of the total AUC, and AUC of the active ingredient from 24 hours to 1 month after the administration calculated from the blood concentration is 10 to 50% of the total AUC, and AUC of the active ingredient from 1 month to 6 months after the administration is 40 to 90% of the total AUC.

A release property of a drug in the sustained-release composition of the present invention is influenced by a loading amount of the drug on preparing, additives such as stearic acid, several above described conditions such as other preparing conditions or a formulation. Therefore, an ideal blood concentration pattern corresponding to the intended sustained-release period can be selected by regulating them as appropriate. Particularly, the regulation of the loading amount of a drug in preparing or the additives such as stearic acid enable a control of a release rate on onset part (from 24 hours to 1 month after administration) and thus a sustained-release preparation showing an ideal blood concentration pattern can be prepared.

While a sustained-release composition of the present invention can be used as a prophylactic/therapeutic agent against various diseases depending on the type of the physiologically active substance contained therein, for example, when the physiologically active substance is an LH-RH derivative, it can be used as a prophylactic/therapeutic agent against a hormone-dependent disease, especially a sex hormone dependent disease such as a sex hormone dependent cancer (e.g., prostate cancer, uterine cancer, breast cancer, and pituitary tumor, etc.), prostatic hyperplasia, endometriosis, uterine fibroid, precocious puberty, dysmenorrhea, amenorrhea, premenstrual syndrome, and multilocular ovarian syndrome, a prophylactic agent against premenopausal breast cancer postoperative recurrence, a prophylactic/therapeutic agent against a disease such as Alzheimer disease or immunodeficiency, and a contraceptive agent (or when a rebound effect after the drug withdrawal is used, a prophylactic/therapeutic agent against a infertility) and the like. In addition, it can be used as a prophylactic/therapeutic agent against a benign or malignant tumor which is sex hormone independent but is LH-RH sensitive.

Therefore, an administration of an effective dose of the present therapeutic/prophylactic agent to mammals can prevent/treat a sex hormone dependent diseases such as a hormone dependent disease, especially sex hormone dependent cancer (e.g., prostate cancer, uterine cancer, breast cancer, and pituitary tumor, etc.), prostatic hyperplasia, endometriosis, uterine fibroid, precocious puberty, dysmenorrhea, amenorrhea, premenstrual syndrome, and multilocular ovarian syndrome and the like, and can prevent conception, furthermore can prevent a premenopausal breast cancer postoperative recurrence.

The present invention is further described with referring to the following Examples and Comparative Examples, which are not intended to restrict the invention.

EXAMPLES

The weight-average molecular weight and the content of each polymer in the following Examples and Comparative Examples are a polystyrene-reduced weight-average molecular weight measured by gel-permeation chromatography (GPC) using a monodispersed polystyrene as a reference substance and a content of each polymer calculated from them. All measurements are performed with a high-speed GPC apparatus (HLC-8120GPC; Tosoh Corporation), using SuperH4000×2 and SuperH2000 (both Tosoh Corporation) as a column, and tetrahydrofuran as a mobile phase at a flow rate of 0.6 mL/min. The detection is conducted based on the differential refractive index.

A measuring method of a blood drug level includes the following methods. For leuprorelin acetate, for example, leuprorelin acetate and 125I-labeled leuprorelin acetate in a serum sample are competitively reacted with a rabbit anti-leuprorelin acetate serum. A goat anti-rabbit γ-globulin serum solution as a second antibody and a normal rabbit serum solution are added to the produced conjugate and reacted, and centrifuged followed by measuring a radioactivity of the precipitate. Leuprorelin acetate concentration in the serum sample is obtained from a calibration curve produced at the same time.

In addition, "leuprorelin acetate" is referred to as "TAP-144" in the Figures.

Example 1

A solution of 3.83 g of DL-lactic acid polymer (weight-average molecular weight: 14,300) in 6.4 g of dichloromethane was added to a solution prepared by adding 4.56 g of methanol to 0.96 g of freeze-dried powder of leuprorelin acetate, dissolving the powder with warming at about 50° C. and then cooling to room temperature (25° C.), and dispersed to prepare the oil phase (O phase). At this point, the loading amount of the drug is 20%. After the O phase was cooled to about 15° C., the solution was poured into 0.8 L of an aqueous solution of 0.1% (w/w) polyvinyl alcohol (EG-40, Nippon Synthetic Chemical Industry Co., Ltd.) pre-adjusted to about 15° C., and was emulsified with a homomixer (Tokushu Kika Kogyo Corporation) to prepare O/W emulsion (turbine rotation frequency: about 7,000 rpm). This O/W emulsion was in-water dried for about 3 hours, and sieved through a sieve having an opening of 75 µm, then, the microcapsules were precipitated and collected using a centrifuge (CR5DL; Hitachi, Ltd.; rotation frequency: about 2,500 rpm). The collected microcapsules were re-dispersed in distilled water. The microcapsules were precipitated and collected by repeating the same centrifuge operation, and then re-dispersed in a small amount of water, and said mixture was recovered in an eggplant-shaped flask together with 0.507 g of mannitol and frozen, then freeze-dried with a freeze drier (DF-01H, ULVAC) to obtain the mixed powder of the leuprorelin-containing microcapsules and mannitol (hereinafter referred to as "microcapsule powder").

The content of leuprorelin acetate in the obtained microcapsule powder was 15.3%, and the yield was about 63%. From the results, it was found that the content of leuprorelin acetate in the microcapsule was 18.0%. The term "the content of leuprorelin acetate in the microcapsule" as referred herein means a calculated rate in which the value calculated by multiplying the total of the charged weight of each raw material (leuprorelin acetate, lactic acid polymer and mannitol) by the yield (hereinafter referred to as "obtained amount"), followed by multiplying by "the content of leuprorelin acetate in the microcapsule powder" is divided by the value calculated by subtracting the amount of mannitol from the obtained amount, that is, it means the value calculated by the following formula:

Content (%) of leuprorelin acetate in the microcapsule=[Total (g) of the charged weight of each raw material]×[Yield (%)]×[Content (%) of leuprorelin acetate in the microcapsule powder]/[[Total (g) of the charged weight of each raw material]×[Yield (%)]−[Amount (g) of mannitol]]

wherein, [Total (g) of the charged weight of each raw material]×[Yield (%)]=[Obtained amount (g)], and corresponds to the content of leuprorelin acetate as the physiologically active substance to the whole microcapsule (the same is applied hereinafter).

Example 2

The microcapsule powder was obtained in the same manner as Example 1 excepting that the temperature after the oil phase (O phase) was prepared and the temperature of 0.1% (w/w) aqueous solution of polyvinyl alcohol (EG-40, Nippon Synthetic Chemical Industry Co., Ltd.) were adjusted to about 20° C.

The content of leuprorelin acetate in the obtained microcapsule powder was 15.1%, and the yield was about 64%. From the results, it was found that the content of leuprorelin acetate in the microcapsule was 17.8%.

Example 3

The microcapsule powder was obtained in the same manner as Example 1 excepting that the temperature after the oil phase (O phase) was prepared and the temperature of 0.1% (w/w) aqueous solution of polyvinyl alcohol (EG-40, Nippon Synthetic Chemical Industry Co., Ltd.) were adjusted to about 25° C.

The content of leuprorelin acetate in the obtained microcapsule powder was 14.3%, and the yield was about 64%. From the results, it was found that the content of leuprorelin acetate in the microcapsule was 16.8%.

Example 4

The microcapsule powder was obtained in the same manner as Example 1 excepting that the temperature after the oil phase (O phase) was prepared and the temperature of 0.1% (w/w) aqueous solution of polyvinyl alcohol (EG-40, Nippon Synthetic Chemical Industry Co., Ltd.) were adjusted to about 30° C.

The content of leuprorelin acetate in the obtained microcapsule powder was 13.4%, and the yield was about 67%. From the results, it was found that the content of leuprorelin acetate in the microcapsule was 15.6%.

Example 5

A solution of 119.5 g of DL-lactic acid polymer (weight-average molecular weight: 14,100) in 200 g of dichloromethane was adjusted to 30° C., and this solution was added to a solution which 142.5 g of methanol was added to 30.0 g of leuprorelin acetate, dissolved with warming at about 40° C. and then cooled to room temperature (25° C.), and said mixture was dispersed to prepare the oil phase (O phase). At this point, the loading amount of the drug is 20%. Then, after the O phase was cooled to about 15° C., the solution was poured into 25 L of an aqueous solution of 0.1% (w/w) polyvinyl alcohol (EG-40, Nippon Synthetic Chemical Industry Co., Ltd.) pre-adjusted to about 15° C., and was emulsified with HOMOMIC LINE FLOW (Tokushu Kika Kogyo Corporation) to prepare the O/W emulsion (turbine rotation frequency: about 7,000 rpm, and circulating pump rotation frequency: about 2,000 rpm.). This O/W emulsion was in-water dried for about 3 hours, and sieved through a sieve having an opening of 75 µm, then, the microcapsules were continuously precipitated with a centrifuge (H-600S; Kokusan Enshinki; rotation frequency: about 2,000 rpm, and flow rate: about 600 ml/min) and collected. The collected microcapsules were re-dispersed in a small amount of distilled water, and sieved through a sieve having an opening of 90 µm, then, 21.1 g of mannitol was added and freeze-dried with freeze drier (DFM-05A-S, ULVAC) to obtain the microcapsule powder. The content of leuprorelin acetate in the obtained microcapsule powder was 14%, and the yield was about 55%. From the results, it was found that the content of leuprorelin acetate in the microcapsule was 18.1%.

Example 6

A solution of 119.5 g of DL-lactic acid polymer (the weight-average molecular weight: 14,100) in 200 g of dichloromethane was adjusted to 30° C., and this solution was added into a solution which 142.5 g of methanol was added to 30.0 g of leuprorelin acetate, dissolved with warming at about 40° C. and then cooled to room temperature (25° C.), and said mixture was dispersed to prepare the oil phase (O phase). At this point, the loading amount of the drug is 20%. Then, after the O phase was cooled to about 20° C., the solution was poured into 25 L of an aqueous solution of 0.1% (w/w) polyvinyl alcohol (EG-40, Nippon Synthetic Chemical Industry Co., Ltd.) pre-adjusted to about 20° C., and was emulsified with HOMOMIC LINE FLOW (Tokushu Kika Kogyo Corporation) to prepare the O/W emulsion (turbine rotation frequency: about 7,000 rpm, and circulating pump rotation frequency: about 2,000 rpm.). This O/W emulsion was in-water dried for about 3 hours, and sieved through a sieve having an opening of 75 µm, then, the microcapsules were continuously precipitated with a centrifuge (H-600S; Kokusan Enshinki; rotation frequency: about 2,000 rpm, and the flow rate: about 600 ml/min) and collected. The collected microcapsules were re-dispersed in a small amount of distilled water, and sieved through a sieve having an opening of 95 μm, then, 17.2 g of mannitol was added and freeze-dried with freeze drier (DFM-05A-S, ULVAC) to obtain the microcapsule powder. The content of leuprorelin acetate in the obtained microcapsule powder was 16.0%, and the yield was about 76%. From the results, it was found that the content of leuprorelin acetate in the microcapsule was 18.5%.

Comparative Example 1

To 0.87 g of leuprorelin acetate, 1 g of distilled water was added to dissolve. To this solution was added a solution of 7.65 g of DL-lactic acid polymer (weight-average molecular weight: 13,900) in 12.8 g of dichloromethane, and lightly dispersed by the hand, then primarily emulsified with Polytron (Kinematica) for about 30 seconds to prepare the W/O emulsion (rotation frequency: about 1,000 rpm). At this point, the loading amount of the drug is 10%. Then, after this W/O emulsion was cooled to about 15° C., the solution was poured into 1.6 L of an aqueous solution of 0.1% (w/w) polyvinyl alcohol (EG-40, Nippon Synthetic Chemical Industry Co., Ltd.) pre-adjusted to about 15° C., and secondarily emulsified with a homomixer (Tokushu Kika Kogyo Corporation) to prepare the W/O/W emulsion (turbine rotation frequency: about 7,000 rpm). This W/O/W emulsion was in-water dried for about 3 hours, and sieved through a sieve having an opening of 75 μm, then, the microcapsules were precipitated and collected using a centrifuge (CR5DL; Hitachi, Ltd.; rotation frequency: about 2,500 rpm). The collected microcapsules were re-dispersed in a small amount of distilled water, added 0.9 g of mannitol and freeze-dried with freeze drier (DF-01H, ULVAC) to obtain the microcapsule powder.

The content of leuprorelin acetate in the obtained microcapsule powder was 7.7%, and the yield was about 62%. From the results, it was found that the content of leuprorelin acetate in the microcapsule was 9.1%.

Comparative Example 2

A solution of 3.83 g of DL-lactic acid polymer (weight-average molecular weight: 13,900) in 6.4 g of dichloromethane was added to a solution which 7.79 g of methanol was added to 1.64 g of the freeze-dried powder of leuprorelin acetate, dissolved with warming at about 50° C. and then cooled to room temperature (25° C.), and said mixture was dispersed to prepare the oil phase (O phase). At this point, the loading amount of the drug is 30%. Then, the O phase was poured into 0.8 L of an aqueous solution of 0.1% (w/w) polyvinyl alcohol (EG-40, Nippon Synthetic Chemical Industry Co., Ltd.) pre-adjusted to about 15° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with centrifuge (CR5DL; Hitachi, Ltd.; rotation frequency: about 2,500 rpm). The collected microcapsules were re-dispersed in distilled water. The microcapsules were precipitated and collected by repeating the same centrifuge operation to collect them, and then re-dispersed in a small amount of water, and said mixture was recovered in an eggplant-shaped flask together with 0.578 g of mannitol and frozen, then freeze-dried with a freeze drier (DF-01H, ULVAC) to obtain the microcapsule powder.

The content of leuprorelin acetate in the obtained microcapsule powder was 16.8%, and the yield was about 74%. From the results, it was found that the content of leuprorelin acetate in the microcapsule was 19.3%.

Comparative Example 3

A solution of 3.83 g of DL-lactic acid polymer (weight-average molecular weight: 14.300) in 6.4 g of dichloromethane was added into a solution prepared by adding 9.80 g of methanol to 2.06 g of the freeze-dried powder of leuprorelin acetate, dissolving the powder with warming at about 50° C. and cooling to room temperature (25° C.), and dispersed to prepare the oil phase (O phase). At this point, the loading amount of the drug is 35%. Then, the O phase was poured into 0.8 L of an aqueous solution of 0.1% (w/w) polyvinyl alcohol (EG-40, Nippon Synthetic Chemical Industry Co., Ltd.) pre-adjusted to about 15° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected using a centrifuge (CR5DL; Hitachi, Ltd.; rotation frequency: about 2,500 rpm). The collected microcapsules were re-dispersed into distilled water. The microcapsules were precipitated by the centrifuge operation to collect them, and then re-dispersed into a small amount of water, and said mixture was recovered in an eggplant-shaped flask together with 0.623 g of mannitol and frozen, then freeze-dried with a freeze drier (DF-01H, ULVAC) to obtain the microcapsule powder.

The content of leuprorelin acetate in the obtained microcapsule powder was 15.0%, and the yield was about 73%. From the results, it was found that the content of leuprorelin acetate in the microcapsule was 17.3%.

Experiment Example 1

Each 29 mg of the microcapsule powder prepared in Example 1 or 34 mg of the microcapsule powder prepared in Comparative Example 1 was suspended in about 0.4 mL of dispersal vehicle, and subcutaneously administered to a rat (4.5 mg dose calculated as leuprorelin acetate), then the leuprorelin acetate concentration in the serum was measured. The transition of blood concentration within 24 hours and up to 13 weeks after the administration is shown in FIG. 1. The calculated results of the maximum concentration (Cmax) and area under the blood concentration-time curve (AUC) within 24 hours after the administration and AUC (of onset part) from 24 hours to one month after the administration are shown in Table 1. As shown in FIG. 1 and Table 1, Cmax and AUC within 24 hours after the administration in Example 1 are lower, and the blood concentration and AUC of onset part are higher than those in Comparative Example 1. That is, a preparation using the O/W method can provide the suppression of the excessive drug release within 24 hours after the administration, and result in the great improvement of the transition of blood concentration on onset part.

TABLE 1

|  | Within 24 hours after the administration | | From 24 hours to one month after the administration |
| --- | --- | --- | --- |
|  | Cmax [ng/mL] | AUC [ng week/mL] | AUC [ng week/mL] |
| Example 1 | 115.5 | 4.0 | 23.1 |
| Comparative Example 1 | 211.9 | 5.1 | 3.2 |

Experiment Example 2

Each entrapment ratio of leuprorelin acetate in the microcapsule powders prepared in Example 1, Comparative Example 2, or Comparative Example 3 was calculated. The results are shown in Table 2. The term "a entrapment ratio of leuprorelin acetate" as herein referred means a rate calculated by dividing "a content of leuprorelin acetate in the microcapsule" by "a loading amount of leuprorelin acetate". As shown in Table 2, the entrapment ratio was greatly reduced in the Comparative Examples wherein the loading amount was 30% or more.

TABLE 2

|  | Example 1 | Comparative Example 2 | Comparative Example 3 |
| --- | --- | --- | --- |
| loading amount of leuprorelin acetate [%] | 20 | 30 | 35 |
| entrapment ratio of leuprorelin acetate [%] | 90.0 | 64.3 | 49.4 |

Experiment Example 3

Figure 2:
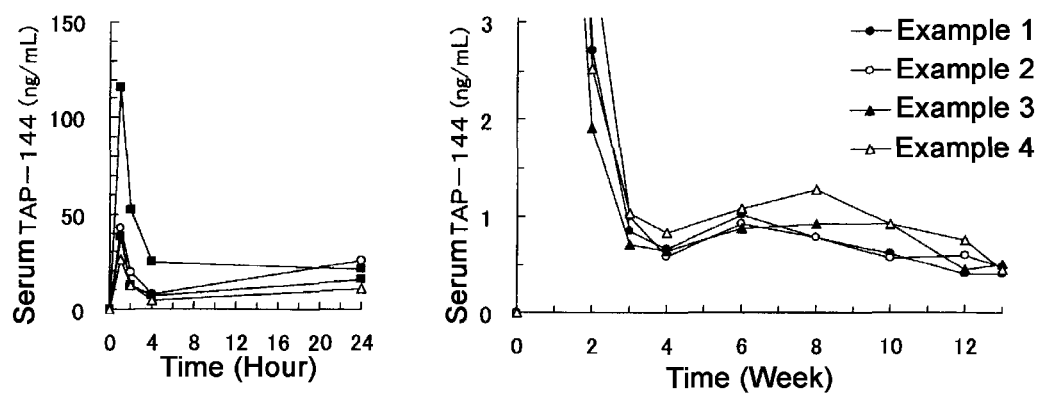
FIG. 2 is a graph showing each transition of blood drug level when the microcapsule powder prepared in Examples 1, 2, 3, and 4 is respectively subcutaneously administered to a rat. The numerical value of the horizontal axis shows time, and the numerical value of the longitudinal axis shows a blood concentration.
Figure 3:
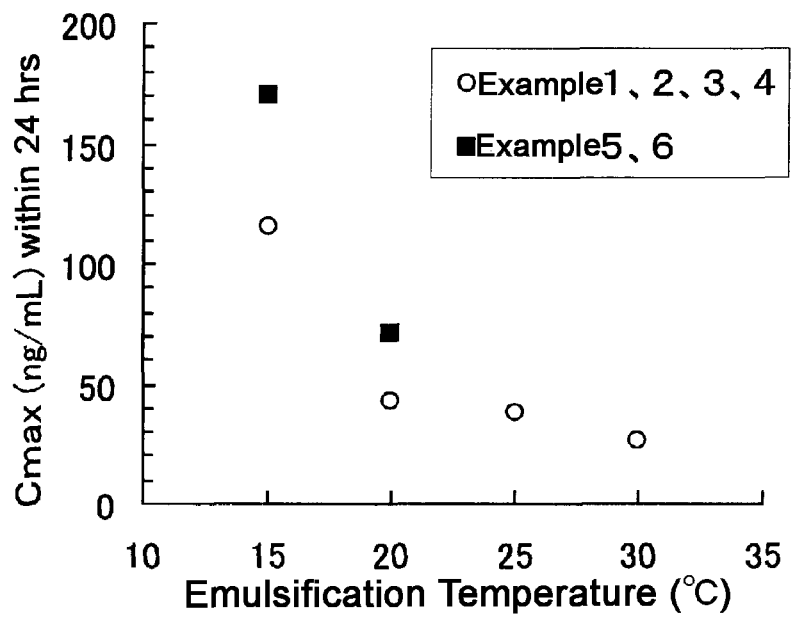
FIG. 3 is a graph showing Cmax calculated from each blood drug level transition when the microcapsule powder prepared in Example 1, Example 2, Example 3, Example 4, Example 5 and Example 6 is respectively subcutaneously administered to a rat. The numerical value of the horizontal axis shows the temperature at an emulsification, and the numerical value of the longitudinal axis shows Cmax.
Figure 4:
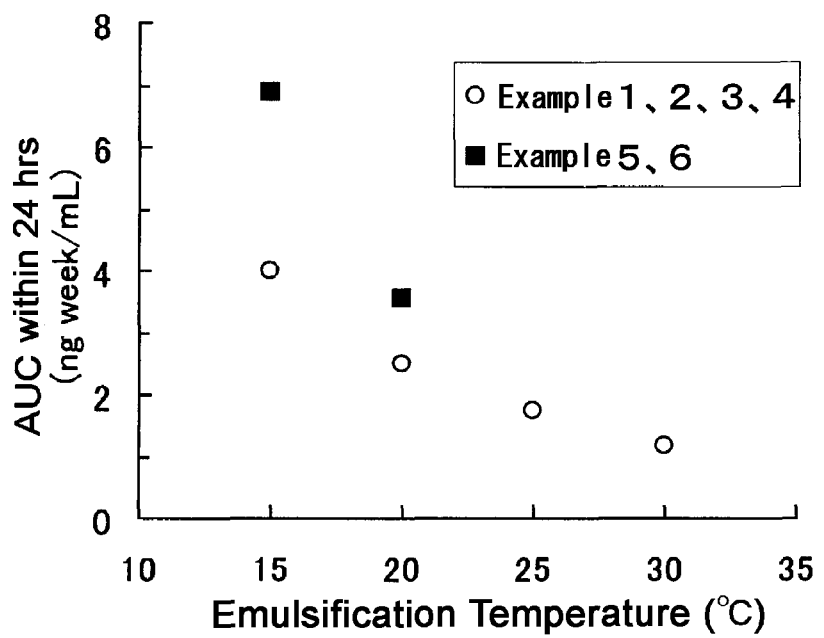
FIG. 4 is a graph showing area under the blood concentration-time curve (AUC) for 24 hours after the administration calculated from each blood drug level transition when the microcapsule powder prepared in Examples 1, 2, 3, 4, 5, and 6 is respectively subcutaneously administered to a rat. The numerical value of the horizontal axis shows the temperature at an emulsification, and the numerical value of the longitudinal axis shows AUC.
Figure 5:
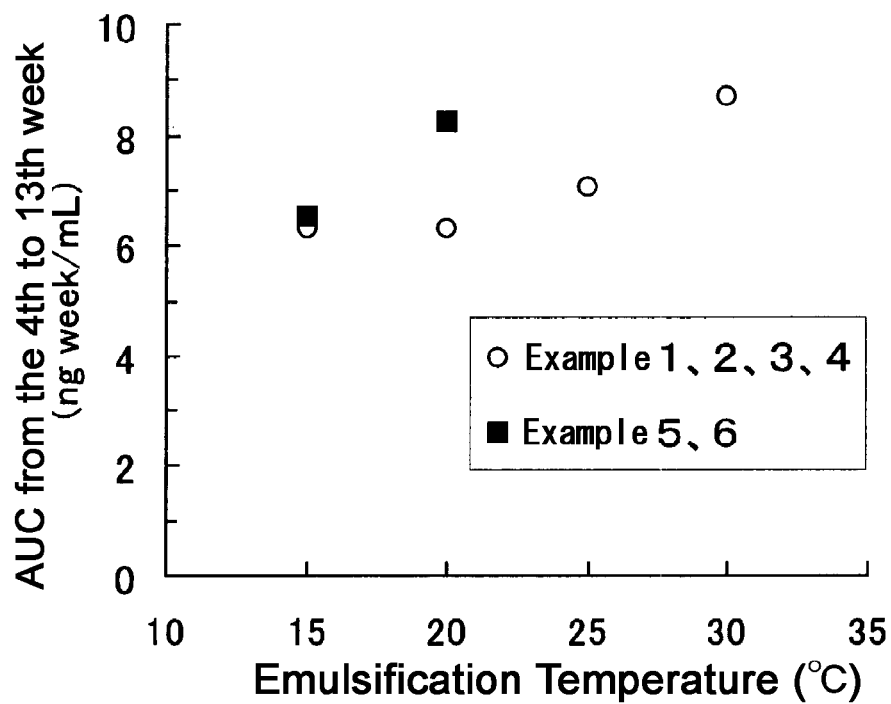
FIG. 5 is a graph showing AUC for a period from 4th weeks to 13th weeks after the administration calculated from each blood drug level transition when the microcapsule powder prepared in Examples 1, 2, 3, 4, 5, and 6 is respectively subcutaneously administered to a rat. The numerical value of the horizontal axis shows the temperature at an emulsification, and the numerical value of the longitudinal axis shows AUC.

Each 29 mg of the microcapsule powder prepared in Example 1, 30 mg of the microcapsule powder prepared in Example 2, 32 mg of the microcapsule powder prepared in Example 3, or 34 mg of the microcapsule powder prepared in Example 4 was suspended in about 0.4 mL of the dispersal vehicle, and subcutaneously administered to a rat (4.5 mg dose calculated as leuprorelin acetate), then the leuprorelin acetate concentration in the serum was measured. The transition of blood concentration within 24 hours and up to 13 weeks after the administration is shown in FIG. 2. The result of the relationship between the emulsification temperature and Cmax within 24 hours after the administration is shown in FIG. 3, the result of the relationship between the emulsification temperature and AUC within 24 hours after the administration is shown in FIG. 4, and the result of the relationship between the emulsification temperature and AUC of the maintenance part (4 weeks or later after the administration) is shown in FIG. 5. As shown in FIGS. 2, 3, and 4, Cmax and AUC within 24 hours after the administration was reduced depending on the emulsification temperature. That is, the raise the emulsification temperature can provide the suppression of initial excessive drug release after administration. Further, as shown in FIGS. 2 and 5, the blood concentration level and AUC of the maintenance part were increased depending on the emulsification temperature. That is, the raise the emulsification temperature can provide the improvement of the transition of blood concentration on the maintenance part.

Experiment Example 4

Figure 6:
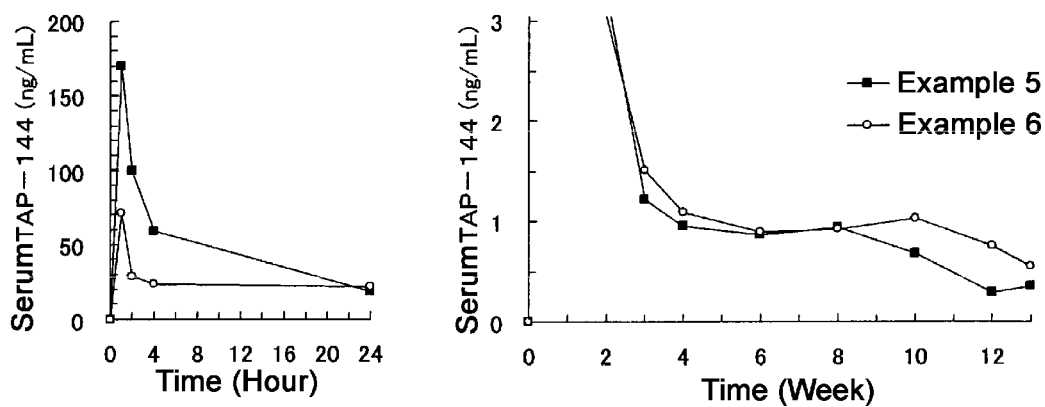
FIG. 6 is a graph showing each blood drug level transition when the microcapsule powder prepared in Example 5 and Example 6 is respectively subcutaneously administered to a rat. The numerical value of the horizontal axis shows time, and the numerical value of the longitudinal axis shows a blood concentration.

Each 32 mg of the microcapsule powder prepared in Example 5 or 28 mg of the microcapsule powder prepared in Example 6 was suspended in about 0.4 mL of the dispersal vehicle, and subcutaneously administered to a rat (4.5 mg dose calculated as leuprorelin acetate), then the leuprorelin acetate concentration in the serum was measured. The transition of blood concentration up to 13 weeks after the administration is shown in FIG. 6. The result of the relationship between the emulsification temperature and Cmax within 24 hours after the administration is shown in FIG. 3, the result of the relationship between the emulsification temperature and AUC within 24 hours after the administration is shown in FIG. 4, and the result of the relationship between the emulsification temperature and AUC of the maintenance part (4 weeks or later after the administration) is shown in FIG. 5. As shown in FIGS. 3, 4, and 6, Cmax and AUC within 24 hours after the administration was reduced depending on the emulsification temperature. That is, the raise the emulsification temperature can provide the initial excessive drug release after the administration. Further, as shown in FIGS. 5 and 6, the blood concentration level and AUC of the maintenance part was increased depending on the emulsification temperature. That is, the raise the emulsification temperature can provide the improvement of the blood concentration transition on the maintenance part.

Experiment Example 5

Figure 7:
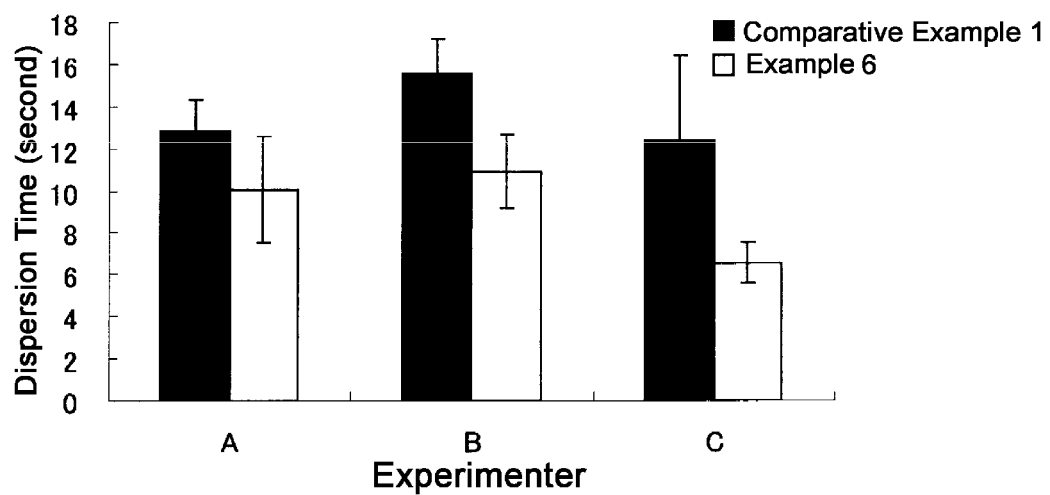
FIG. 7 is a graph showing each dispersion time when the microcapsule powder prepared in Example 6 and Comparative Example 1 is respectively suspended into a dispersion medium. The horizontal axis shows the experimenter (total 3), and the numerical value of the longitudinal axis shows the time for dispersion.

Each microcapsule powder (45 mg calculated as leuprorelin acetate) prepared in Example 6 or Comparative Example 1 and the dispersing solvent (1 mL volume) was mixed, and lightly dispersed by the hand to homogeneously disperse. The time from the mixing was initiated until the mixture was uniformly dispersed was measured, respectively. The result is shown in FIG. 7. The mixture of Example 6 was dispersed in a shorter time than that of Comparative Example 1.

Comparative Example 4

To 2.4 g of leuprorelin acetate, 11.4 g of methanol was added to dissolve with warming at about 40° C., then this solution was adjusted to 30° C. To this solution, a solution of 9.6 g of DL-lactic acid polymer (weight-average molecular weight: 21,700) in 16.8 g of dichloromethane was added, and dispersed to prepare a homogeneous oil phase (O phase). At this point, the loading amount of the drug is 20%. Then, the O phase was poured into 2 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, the mixture was re-centrifuged to precipitate the microcapsules. After the supernatant was removed, 1.27 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 15.3%, and the yield was about 65%. From the results, it was found that the content of leuprorelin acetate in the microcapsule was 17.9%. The term "the content of leuprorelin acetate in the microcapsule" as referred herein means a calculated rate in which the value calculated by multiplying the total of the charged weight of each raw material (leuprorelin acetate, lactic acid polymer and mannitol) by the yield (hereinafter referred to as "obtained amount"), followed by multiplying by "the content of leuprorelin acetate in the microcapsule powder" is divided by the value calculated by subtracting the amount of mannitol from the obtained amount, and corresponds to the content of leuprorelin acetate as the physiologically active substance to the whole microcapsule (same is applied hereinafter).

Comparative Example 5

To 1.2 g of leuprorelin acetate, 5.7 g of methanol was added to dissolve with warming at about 40° C., then this solution was adjusted to 30° C. To this solution, a solution of 4.8 g of DL-lactic acid polymer (weight-average molecular weight: 26,100) in 8.4 g of dichloromethane was added, and to blend with stirring to prepare a homogeneous oil phase (O phase). At this point, the loading amount of the drug is 19%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). The O/W emulsion was in-water dried for about 3 hours, and sieved through a sieve having an opening of 75 µm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 14.7%, and the yield was about 54%. From the results, it was found that the content of leuprorelin acetate in the microcapsule was 17.9%.

Comparative Example 6

To 1.35 g of leuprorelin acetate, 6.41 g of methanol was added to dissolve with warming at about 40° C., then this solution was adjusted to 30° C. To this solution, a solution of 4.65 g of DL-lactic acid polymer (weight-average molecular weight: 21,700) in 8.14 g of dichloromethane was added, and to blend with stirring to prepare a homogeneous oil phase (O phase). At this point, the loading amount of the drug is 22.5%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare a O/W emulsion (turbine rotation frequency: about 7,000 rpm). The O/W emulsion was in-water dried for about 3 hours, and sieved through a sieve having an opening of 75 µm, then, the microcapsules were precipitated and collected with a centrifuge (CR5DL; Hitachi, Ltd.; rotation frequency: about 3,000 rpm). Distilled water was added to the microcapsules to wash, then the mixture was centrifuged again to precipitate the microcapsules. After the supernatant was removed, 0.635 g of mannitol was added thereto, and the mixture was dispersed in a small amount of distilled water. The dispersion was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 16.8%, and the yield was about 55%. From the results, it was found that the content of leuprorelin acetate in the microcapsule was 20.3%.

Example 7

To 1.14 g of leuprorelin acetate and 0.269 g of stearic acid, 5.7 g of methanol was added to dissolve with warming at about 40° C., then this solution was adjusted to 30° C. To this solution, a solution of 4.53 g of DL-lactic acid polymer (weight-average molecular weight: 21,700) in 7.93 g of dichloromethane was added, and to blend with stirring to prepare a homogeneous oil phase (O phase). At this point, the loading amount of the drug is 19%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 µm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 15.4%, and the yield was about 57%. From the results, it was found that the content of leuprorelin acetate in the microcapsule was 18.5%. The term "the content of leuprorelin acetate in the microcapsule" as herein referred means a calculated rate in which the value calculated by multiplying the total of the charged weight of each raw material (leuprorelin acetate, lactic acid polymer, stearic acid and mannitol) by the yield (hereinafter referred to as "obtained amount"), followed by multiplying by "the content of leuprorelin acetate in the microcapsule powder" is divided by the value calculated by subtracting the amount of mannitol from the obtained amount, and corresponds to the content of leuprorelin acetate as the physiologically active substance to the whole microcapsule (the same is applied hereinafter).

Example 8

To 1.14 g of leuprorelin acetate and 0.269 g of stearic acid, 5.7 g of methanol was added to dissolve with warming at about 40° C., then this solution was adjusted to 30° C. To this solution, a solution of 4.53 g of DL-lactic acid polymer (weight-average molecular weight: 26,100) in 7.93 g of dichloromethane was added, and to blend with stirring to prepare a homogeneous oil phase (O phase). At this point, the loading amount of the drug is 19%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then said mixture was recentrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 14.7%, and the yield was about 56%. From the results, it was found that the content of leuprorelin acetate in the microcapsule was 17.8%.

Example 9

To 1.29 g of leuprorelin acetate and 0.3025 g of stearic acid, 6.413 g of methanol was added to dissolve with warming at about 40° C., then this solution was adjusted to 30° C. To this solution, a solution of 4.347 g of DL-lactic acid polymer (weight-average molecular weight: 21,700) in 7.608 g of dichloromethane was added, and to blend with stirring to prepare a homogeneous oil phase (O phase). At this point, the loading amount of the drug is 21.7%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 17.1%, and the yield was about 58%. From the results, it was found that the content of leuprorelin acetate in the microcapsule was 20.5%.

Example 10

To 1.29 g of leuprorelin acetate and 0.3025 g of stearic acid, 6.413 g of methanol was added to dissolve with warming at about 40° C., then this solution was adjusted to 30° C. To this solution, a solution of 4.347 g of DL-lactic acid polymer (weight-average molecular weight: 26,100) in 7.608 g of dichloromethane was added, and to blend with stirring to prepare a homogeneous oil phase (O phase). At this point, the loading amount of the drug is 21.7%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 15.2%, and the yield was about 59%. From the results, it was found that the content of leuprorelin acetate in the microcapsule was 18.2%.

Example 11

To 1.35 g of leuprorelin acetate and 0.079 g of stearic acid (0.25-fold mole of leuprorelin acetate), 6.4 g of methanol was added to dissolve with warming at about 40° C., then this solution was adjusted to 30° C. To this solution, a solution of 4.57 g of DL-lactic acid polymer (weight-average molecular weight: 21,800) in 8.0 g of dichloromethane was added, and to blend with stirring to prepare a homogeneous oil phase (O phase). At this point, the loading amount of the drug is 22.5%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 18.1%, and the yield was about 68%. From the results, it was found that the content of leuprorelin acetate in the microcapsule was 21.1%.

Example 12

To 1.35 g of leuprorelin acetate and 0.157 g of stearic acid (0.5-fold mole of leuprorelin acetate), 6.4 g of methanol was added to dissolve with warming at about 40° C., then this solution was adjusted to 30° C. To this solution, a solution of 4.5 g of DL-lactic acid polymer (weight-average molecular weight: 21,800) in 7.9 g of dichloromethane was added, and to blend with stirring to prepare a homogeneous oil phase (O phase). At this point, the loading amount of the drug is 22.5%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, the said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 17.5%, and the yield was about 56%. From the results, it was found that the content of leuprorelin acetate in the microcapsule was 21.1%.

Example 13

To 1.35 g of leuprorelin acetate and 0.315 g of stearic acid (1-fold mole of leuprorelin acetate), 6.4 g of methanol was added to dissolve with warming at about 40° C., then this solution was adjusted to 30° C. To this solution, a solution of 4.34 g of DL-lactic acid polymer (weight-average molecular weight: 21,800) in 7.6 g of dichloromethane was added, and to blend with stirring to prepare a homogeneous oil phase (O phase). At this point, the loading amount of the drug is 22.5%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 16.7%, and the yield was about 52%. From the results, it was found that the content of leuprorelin acetate in the microcapsule was 20.5%.

Example 14

To 1.35 g of leuprorelin acetate and 0.471 g of stearic acid (1.5-fold mole of leuprorelin acetate), 6.4 g of methanol was added to dissolve with warming at about 40° C., then this solution was adjusted to 30° C. To this solution, a solution of 4.19 g of DL-lactic acid polymer (weight-average molecular weight: 21,800) in 7.34 g of dichloromethane was added, and to blend with stirring to prepare a homogeneous oil phase (O phase). At this point, the loading amount of the drug is 22.5%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 17.1%, and the yield was about 73%. From the results, it was found that the content of leuprorelin acetate in the microcapsule was 19.7%.

Example 15

To 1.23 g of leuprorelin acetate and 0.287 g of stearic acid (1-fold mole of leuprorelin acetate), 5.8 g of methanol was added to dissolve with warming at about 40° C., then this solution was adjusted to 30° C. To this solution, a solution of 4.49 g of DL-lactic acid polymer (weight-average molecular weight: 21,800) in 7.9 g of dichloromethane was added, and to blend with stirring to prepare a homogeneous oil phase (O phase). At this point, the loading amount of the drug is 20.5%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 15.8%, and the yield was about 66%. From the results, it was found that the content of leuprorelin acetate in the microcapsule was 18.5%.

Example 16

To 1.29 g of leuprorelin acetate and 0.300 g of stearic acid (1-fold mole of leuprorelin acetate), 6.1 g of methanol was added to dissolve with warming at about 40° C., then this solution was adjusted to 30° C. To this solution, a solution of 4.42 g of DL-lactic acid polymer (weight-average molecular weight: 21,800) in 7.7 g of dichloromethane was added, and to blend with stirring to prepare a homogeneous oil phase (O phase). At this point, the loading amount of the drug is 21.5%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 15.9%, and the yield was about 56%. From the results, it was found that the content of leuprorelin acetate in the microcapsule was 19.2%.

Example 17

To 1.41 g of leuprorelin acetate and 0.328 g of stearic acid (1-fold mole of leuprorelin acetate), 6.7 g of methanol was added to dissolve with warming at about 40° C., then this solution was adjusted to 30° C. To this solution, a solution of 4.27 g of DL-lactic acid polymer (weight-average molecular weight: 21,800) in 7.5 g of dichloromethane was added, and to blend with stirring to prepare a homogeneous oil phase (O phase). At this point, the loading amount of the drug is 23.5%. Then, the O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 17.0%, and the yield was about 71%. From the results, it was found that the content of leuprorelin acetate in the microcapsule was 19.6%.

Example 18

To 1.47 g of leuprorelin acetate and 0.342 g of stearic acid (1-fold mole of leuprorelin acetate), 7.0 g of methanol was added to dissolve with warming at about 40° C., then this solution was adjusted to 30° C. To this solution, a solution of 4.20 g of DL-lactic acid polymer (weight-average molecular weight: 21,800) in 7.4 g of dichloromethane was added, and to blend with stirring to prepare a homogeneous oil phase (O phase). At this point, the loading amount of the drug is 24.5%. Then, the O phase was poured into 1 L of an aqueous solution of 0.1% (w/w) of polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare the O/W emulsion (turbine rotation frequency: about 7,000 rpm). This O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). Distilled water was added to the microcapsules to wash, then, said mixture was re-centrifuged to precipitate the microcapsules. After the supernatant was removed, 0.635 g of mannitol was added to this mixture to disperse in a small amount of distilled water, and said mixture was recovered in an eggplant-shaped flask. This dispersion was frozen, and freeze-dried with a freeze drier (DF-01H, ULVAC) to obtain the microcapsule powder.

The content of leuprorelin acetate in the obtained microcapsule powder was 16.3%, and the yield was about 77%. From the results, it was found that the content of leuprorelin acetate in the microcapsule was 18.6%.

Example 19

To 33.75 g of leuprorelin acetate and 7.56 g of stearic acid (1-fold mole of leuprorelin acetate), 160.33 g of methanol was added to dissolve with warming at about 40° C., then this solution was adjusted to 30° C. To this solution, a solution of 108.68 g of DL-lactic acid polymer (weight-average molecular weight: 21,800) in 190.2 g of dichloromethane was added, and to blend with stirring to prepare a homogeneous oil phase (O phase). At this point, the loading amount of the drug is 22.5%. Then, after the O phase was adjusted to about 30° C., the O phase was poured into 25 L of an aqueous solution of 0.1% (w/w) polyvinyl alcohol (EG-40, Nippon Synthetic Chemical Industry Co., Ltd.) pre-adjusted to about 18° C., and was emulsified with a HOMOMIC LINE FLOW (Tokushu Kika Kogyo Corporation) to prepare the O/W emulsion (turbine rotation frequency: about 7,000 rpm, and the circulating pump rotation frequency: about 2,000 rpm.). This O/W emulsion was in-water dried for about 3 hours, and sieved through a sieve having an opening of 75 μm, then, the microcapsules were continuously precipitated with a centrifuge (H-600S; Kokusan Enshinki; rotation frequency: about 2,000 rpm, and the flow rate: about 600 ml/min) and collected. The collected microcapsules were re-dispersed in a small amount of distilled water, and sieved through a sieve having an opening of 90 μm, then, 17.2 g of mannitol was added and freeze-dried with freeze drier (DFM-05A-S, ULVAC) to obtain the microcapsule powder. The content of leuprorelin acetate in the obtained microcapsule powder was 18.2%, and the yield was about 80%. From the results, it was found that the content of leuprorelin acetate in the microcapsule was 20.9%.

Example 20

To 30.0 g of leuprorelin acetate and 6.725 g of stearic acid (1-fold mole of leuprorelin acetate), 142.5 g of methanol was added to dissolve with warming at about 40° C., then this solution was adjusted to 30° C. To this solution, a solution of 113.28 g of DL-lactic acid polymer (weight-average molecular weight: 21,800) in 198.23 g of dichloromethane was added, and to blend with stirring to prepare a homogeneous oil phase (O phase). At this point, the loading amount of the drug is 20.0%. Then, after the O phase was adjusted to about 30° C., the O phase was poured into 25 L of an aqueous solution of 0.1% (w/w) polyvinyl alcohol (EG-40, Nippon Synthetic Chemical Industry Co., Ltd.) pre-adjusted to about 18° C., and was emulsified with a HOMOMIC LINE FLOW (Tokushu Kika Kogyo Corporation) to prepare the O/W emulsion (turbine rotation frequency: about 7,000 rpm, and the circulating pump rotation frequency: about 2,000 rpm.). This O/W emulsion was in-water dried for about 3 hours, and sieved through a sieve having an opening of 75 μm, then, the microcapsules were continuously precipitated with a centrifuge (H-600S; Kokusan Enshinki; rotation frequency: about 2,000 rpm, and the flow rate: about 600 ml/min) and collected. The collected microcapsules were re-dispersed in a small amount of distilled water, and sieved through a sieve having an opening of 90 μm, then, 17.2 g of mannitol was added and freeze-dried with freeze drier (DFM-05A-S, ULVAC) to obtain the microcapsule powder. The content of leuprorelin acetate in the obtained microcapsule powder was 16.6%, and the yield was about 80%. From the results, it was found that the content of leuprorelin acetate in the microcapsule was 19.0%.

Example 21

To 22.68 g of leuprorelin acetate and 5.08 g of stearic acid (1-fold mole of leuprorelin acetate), 107.7 g of methanol was added to dissolve with warming at about 40° C., then this solution was adjusted to 30° C. To this solution, a solution of 80.24 g of DL-lactic acid polymer (weight-average molecular weight: 26,100) in 140.4 g of dichloromethane was added, and to blend with stirring to prepare a homogeneous oil phase (O phase). At this point, the loading amount of the drug is 21.0%. Then, after the O phase was adjusted to about 30° C., the O phase was poured into 18 L of an aqueous solution of 0.1% (w/w) polyvinyl alcohol (EG-40, Nippon Synthetic Chemical Industry Co., Ltd.) pre-adjusted to about 18° C., and was emulsified with a HOMOMIC LINE FLOW (Tokushu Kika Kogyo Corporation) to prepare the O/W emulsion (turbine rotation frequency: about 7,000 rpm, and the circulating pump rotation frequency: about 2,000 rpm.). This O/W emulsion was in-water dried for about 3 hours, and sieved through a sieve having an opening of 75 μm, then, the microcapsules were continuously precipitated with a centrifuge (H-600S; Kokusan Enshinki; rotation frequency: about 2,000 rpm, and the flow rate: about 600 ml/min) and collected. The collected microcapsules were re-dispersed in a small amount of distilled water, and sieved through a sieve having an opening of 90 μm, then, 13.3 g of mannitol was added and freeze-dried with freeze drier (DFM-05A-S, ULVAC) to obtain the microcapsule powder. The content of leuprorelin acetate in the obtained microcapsule powder was 16.5%, and the yield was about 73%. From the results, it was found that the content of leuprorelin acetate in the microcapsule was 19.4%.

Example 22

To 31.5 g of leuprorelin acetate, 130.08 g of methanol was added to dissolve with warming at about 40° C., then this solution was adjusted to 30° C. To this solution, a solution of 111.44 g of DL-lactic acid polymer (weight-average molecular weight: 26,300) and 7.06 g of stearic acid (1-fold mole of leuprorelin acetate) in the mixture of 195.0 g of dichloromethane and 19.50 g of methanol was added, and to blend with stirring to prepare a homogeneous oil phase (O phase). At this point, the loading amount of the drug is 21.0%. After the O phase was adjusted to about 30° C., the O phase was poured into 25 L of an aqueous solution of 0.1% (w/w) polyvinyl alcohol (EG-40, Nippon Synthetic Chemical Industry Co., Ltd.) pre-adjusted to about 18° C., and was emulsified with a HOMOMIC LINE FLOW (Tokushu Kika Kogyo Corporation) to prepare the O/W emulsion (turbine rotation frequency: about 7,000 rpm, and the circulating pump rotation frequency: about 2,000 rpm.). This O/W emulsion was in-water dried for about 3 hours, and sieved through a sieve having an opening of 75 μm, then, the microcapsules were continuously precipitated with a centrifuge (H-600S; Kokusan Enshinki; rotation frequency: about 2,000 rpm, and the flow rate: about 600 ml/min) and collected. The collected microcapsules were re-dispersed in a small amount of distilled water, and sieved through a sieve having an opening of 90 μm, then, 17.2 g of mannitol was added and freeze-dried with freeze drier (DFM-05A-S, ULVAC) to obtain the microcapsule powder. The content of leuprorelin acetate in the obtained microcapsule powder was 17.5%, and the yield was about 78%. From the results, it was found that the content of leuprorelin acetate in the microcapsule was 20.2%.

Example 23

To 33.75 g of leuprorelin acetate, 141.31 g of methanol was added to dissolve with warming at about 40° C., then this solution was adjusted to 30° C. To this solution, a solution of 108.68 g of DL-lactic acid polymer (weight-average molecular weight: 22,100) and 7.56 g of stearic acid (1-fold mole of leuprorelin acetate) in the mixture of 190.2 g of dichloromethane and 19.02 g of methanol was added, and to blend with stirring to prepare a homogeneous oil phase (O phase). At this point, the loading amount of the drug is 22.5%. After the O phase was adjusted to about 30° C., the O phase was poured into 25 L of an aqueous solution of 0.1% (w/w) polyvinyl alcohol (EG-40, Nippon Synthetic Chemical Industry Co., Ltd.) pre-adjusted to about 18° C., and was emulsified with a HOMOMIC LINE FLOW (Tokushu Kika Kogyo Corporation) to prepare the O/W emulsion (turbine rotation frequency: about 7,000 rpm, and the circulating pump rotation frequency: about 2,000 rpm.). This O/W emulsion was in-water dried for about 3 hours, and sieved through a sieve having an opening of 75 μm, then, the microcapsules were continuously precipitated with a centrifuge (H-600S; Kokusan Enshinki; rotation frequency: about 2,000 rpm, and the flow rate: about 600 ml/min) and collected. The collected microcapsules were re-dispersed in a small amount of distilled water, and sieved through a sieve having an opening of 90 μm, then, 17.2 g of mannitol was added and freeze-dried with freeze drier (DFM-05A-S, ULVAC) to obtain the microcapsule powder. The content of leuprorelin acetate in the obtained microcapsule powder was 18.4%, and the yield was about 77%. From the results, it was found that the content of leuprorelin acetate in the microcapsule was 21.2%.

Example 24

To 30 g of leuprorelin acetate, 122.68 g of methanol was added to dissolve with warming at about 40° C., then this solution was adjusted to 30° C. To this solution, a solution of 113.28 g of DL-lactic acid polymer (weight-average molecular weight: 22,100) and 6.725 g of stearic acid (1-fold mole of leuprorelin acetate) in the mixture of 198.2 g of dichloromethane and 19.82 g of methanol was added, and mixed with stirring to prepare a homogeneous oil phase (O phase). At this point, the loading amount of the drug is 20%.

After the O phase was adjusted to about 30° C., the O phase was poured into 25 L of an aqueous solution of 0.1% (w/w) polyvinyl alcohol (EG-40, Nippon Synthetic Chemical Industry Co., Ltd.) pre-adjusted to about 18° C., and was emulsified with a HOMOMIC LINE FLOW (Tokushu Kika Kogyo Corporation) to prepare an O/W emulsion (turbine rotation frequency: about 7,000 rpm, and the circulating pump rotation frequency: about 2,000 rpm). This O/W emulsion was in-water dried for about 3 hours, and sieved through a sieve having an opening of 75 μm, then, the microcapsules were continuously precipitated with a centrifuge (H-600S; Kokusan Enshinki; rotation frequency: about 2,000 rpm, the flow rate: about 600 ml/min) and collected. The collected microcapsules were dispersed again in a small amount of distilled water, and sieved through a sieve having an opening of 90 μm. Then, 19.9 g of mannitol was added thereto, and freeze-dried with freeze drier (DFM-05A-S, ULVAC) to obtain the microcapsule powder. The content of leuprorelin acetate in the obtained microcapsule powder was 15.4%, and the yield was about 66%. From the results, it was found that the content of leuprorelin acetate in the microcapsule was 18.7%.

Example 25

To 1.35 g of leuprorelin acetate and 0.907 g of stearic acid (3-fold mole of leuprorelin acetate) was added 6.4 g of methanol to dissolve with warming at about 40° C., then this solution was adjusted to 30° C. To this solution was added a solution of 3.74 g of DL-lactic acid polymer (weight-average molecular weight: 21,800) in 6.5 g of dichloromethane, and mixed with stirring to prepare a homogeneous oil phase (O phase). At this point, the loading amount of the drug is 22.5%. This O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare an O/W emulsion (turbine rotation frequency: about 7,000 rpm). The O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). To the microcapsules was added distilled water to wash, and was centrifuged again to precipitate. After removing the supernatant, 0.635 g of mannitol was added thereto, and the mixture was dispersed with a small amount of distilled water. The dispersion was recovered in an eggplant-shaped flask. This dispersion was frozen, and freeze-dried with a freeze drier (DF-01H, ULVAC) to obtain the microcapsule powder. The content of leuprorelin acetate in the obtained microcapsule powder was 9.6%, and the yield was about 44%. From the results, it was found that the content of leuprorelin acetate in the microcapsule was 12.2%.

Example 26

To 1.35 g of leuprorelin acetate and 1.513 g of stearic acid (5-fold mole of leuprorelin acetate) was added 6.4 g of methanol to dissolve with warming at about 40° C., then this solution was adjusted to 30° C. To this solution was added a solution of 3.14 g of DL-lactic acid polymer (weight-average molecular weight: 21,800) in 5.5 g of dichloromethane, and mixed with stirring to prepare a homogeneous oil phase (O phase). At this point, the loading amount of the drug is 22.5%. This O phase was poured into 1 L of an aqueous solution of 0.1% (w/w) polyvinyl alcohol (EG-40, Nippon Synthetic Chemical Industry Co., Ltd.) pre-adjusted to about 18° C., and was emulsified with a homomixer (Tokushu Kika Kogyo Corporation) to prepare an O/W emulsion (turbine rotation frequency: about 7,000 rpm). The O/W emulsion was in-water dried for about 3 hours, and sieved through a sieve having an opening of 75 μm, then, the microcapsules were precipitated and collected with a centrifuge (CR5DL; Hitachi, Ltd.; rotation frequency: about 3,000 rpm). To the microcapsules was added distilled water to wash, and was centrifuged again to precipitate. After removing the supernatant, 0.635 g of mannitol was added thereto, and the mixture was dispersed with a small amount of distilled water. The dispersion was recovered in an eggplant-shaped flask. This dispersion was frozen, and freeze-dried with a freeze drier (DF-01H, ULVAC) to obtain the microcapsule powder. The content of leuprorelin acetate in the obtained microcapsule powder was 5.3%, and the yield was about 53%. From the results, it was found that the content of leuprorelin acetate in the microcapsule was 6.5%.

Experiment Example 6

Figure 8:
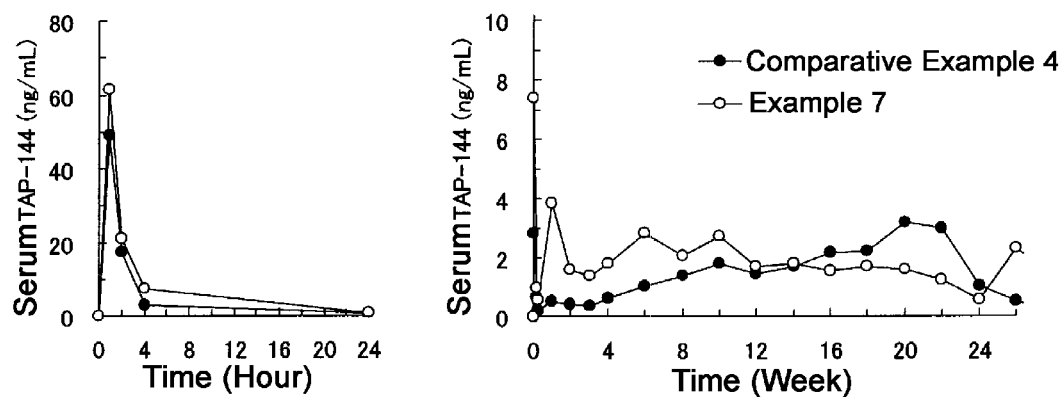
FIG. 8 is a graph showing each blood drug level transition when the microcapsule powder prepared in Example 7 and Comparative Example 4 is respectively subcutaneously administered to a rat. The numerical value of the horizontal axis shows time, and the numerical value of the longitudinal axis shows the blood concentration.

Each 59 mg of the microcapsule powder prepared in Comparative Example 4 or 59 mg of the microcapsule powder prepared in Example 7 was suspended in about 0.4 mL of the dispersal vehicle, and subcutaneously administered to a rat (9 mg dose calculated as leuprorelin acetate), then the leuprorelin acetate concentrations in the serum were measured. The transition of blood concentration is shown in FIG. 8. For the period from 1 week to 10 weeks after the administration, the blood concentration level of Example 7 was greatly higher than that of Comparative Example 2. That is, an addition of stearic acid can result in the improvement of the release rate of the drug, and can provide the improvement of the blood concentration levels on onset part (from 24 hours to 1 month after the administration) and maintenance part (1 month or later after the administration).

Experiment Example 7

Figure 9:
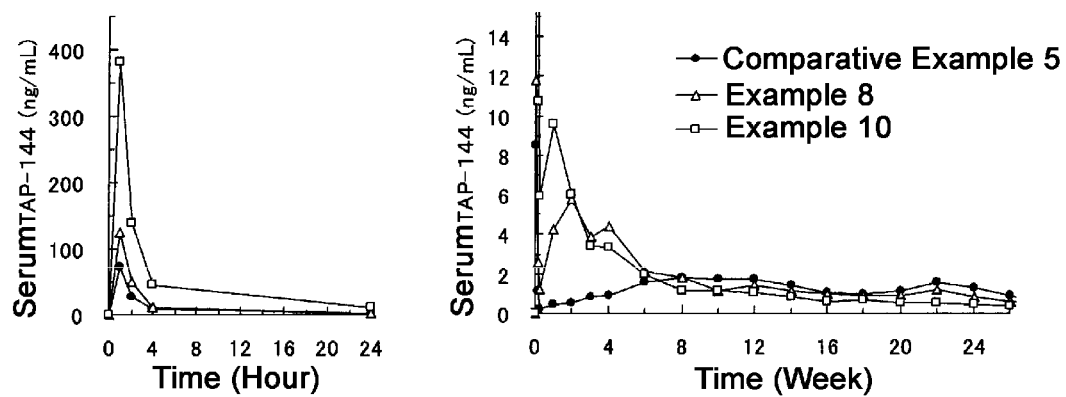
FIG. 9 is a graph showing each blood drug level transition when the microcapsule powder prepared in Examples 8 and 10, and Comparative Example 5 is respectively subcutaneously administered to a rat. The numerical value of the horizontal axis shows time, and the numerical value of the longitudinal axis shows the blood concentration.

Each 61 mg of the microcapsule powder prepared in Comparative Example 5, 61 mg of the microcapsule powder prepared in Example 8, or 59 mg of the microcapsule powder prepared in Example 10 was suspended in about 0.4 mL of the dispersal vehicle, and subcutaneously administered to a rat (9 mg dose calculated as leuprorelin acetate), then the leuprorelin acetate concentrations in the serum were measured. The transition of blood concentration is shown in FIG. 9. In the period 4 weeks after the administration, the blood concentration level of Example 8 and Example 10 was greatly higher than that of Comparative Example 3. Additionally, in the hollow-section in second day after the administration observed in Example 8, Example 10 maintained the high level, and showed more favorable blood concentration pattern. That is, a control of an additive amount of stearic acid and a loading dose of the drug can provide the control of the release rate on onset part (from 24 hours to 1 month after the administration) and the achievement of the ideal blood concentration pattern.

Experiment Example 8

The entrapment ratios of leuprorelin acetate in the microcapsule powders prepared in Example 15, Example 16, Example 13, Example 17 and Example 18 were calculated, respectively. The results are shown in Table 3. The term "a entrapment ratio of leuprorelin acetate" as herein referred means a rate calculated by dividing "a content of leuprorelin acetate in the microcapsule" by "a loading amount of leuprorelin acetate". As shown in Table 3, a slightly decreasing tendency of the entrapment ratio was observed after the loading amount exceeded 23.5%.

TABLE 3

| | Example 15 | Example 16 | Example 13 | Example 17 | Example 18 |
|---|---|---|---|---|---|
| Mole ratio of added stearic acid to leuprorelin acetate | 1 | 1 | 1 | 1 | 1 |
| Loading amount of leuprorelin acetate [%] | 20.5 | 21.5 | 22.5 | 23.5 | 24.5 |
| entrapment ratio of leuprorelin acetate [%] | 90.2 | 89.3 | 91.0 | 83.7 | 76.1 |

Experiment Example 9

The entrapment ratios of leuprorelin acetate in the microcapsule powders prepared in Comparative Example 4, Example 11, Example 12, Example 13, Example 14, Example 25 and Example 26 were calculated, respectively. The results are shown in Table 4. A decreasing tendency of entrapment ratio was observed after the mole ratio of the added stearic acid to leuprorelin acetate exceeded 1.5.

TABLE 4

| | Comparative Example 4 | Example 11 | Example 12 | Example 13 | Example 14 | Example 25 | Example 26 |
|---|---|---|---|---|---|---|---|
| Mole ratio of added stearic acid to leuprorelin acetate | 0 | 0.25 | 0.5 | 1.0 | 1.5 | 3.0 | 5.0 |
| Loading amount of leuprorelin acetate [%] | 22.5 | 22.5 | 22.5 | 22.5 | 22.5 | 22.5 | 22.5 |
| Entrapment ratio of leuprorelin acetate [%] | 90.4 | 93.6 | 93.9 | 91.0 | 87.6 | 54.1 | 28.8 |

Experiment Example 10

59 mg of the microcapsule powder prepared in Comparative Example 4, 54 mg of the microcapsule powder prepared in Comparative Example 6, 50 mg of the microcapsule powder prepared in Example 19, 54 mg of the microcapsule powder prepared in Example 20 and 55 mg of the microcapsule powder prepared in Example 21 were suspended in about 0.4 mL of dispersal vehicle, respectively, and subcutaneously administered to a rat (9 mg dose as leuprorelin acetate, respectively), then the leuprorelin acetate concentrations in the serum were measured. The results of the maximum blood level (Cmax) and AUC within 24 hours after the administration, AUC from 24-hour to one month after the administration (onset part) and serum concentration of the sixth month after the administration are shown in Table 5. As seen from Table 5, the preparation of Examples 19, 20 and 21 wherein the loading amount of the drug is about 20 to 22.5% and stearic acid is contained had a high blood level and AUC for the onset part, compared to the preparation of Comparative Examples 4 and 6 wherein the loading amount of the drug is about 20 to 22.5% and stearic acid is not contained. On the other hand, the drug was detected from blood even at 6 months after the administration, and it is confirmed that the drug is being released over a long period of time. That is, the transition of blood level in onset part could be improved significantly by containing stearic acid.

TABLE 5

| | within 24 hours after the administration | | 24-hour to one month after the administration | sixth month after the administration |
|---|---|---|---|---|
| | Cmax [ng/mL] | AUC [ng week/mL] | AUC [ng week/mL] | serum concentration [ng/mL] |
| Comparative Example 4 | 49.07 | 0.67 | 1.71 | 1.02 |
| Comparative Example 6 | 129.97 | 1.56 | 2.30 | 1.17 |
| Example 19 | 220.65 | 3.48 | 15.01 | 0.39 |
| Example 20 | 132.63 | 1.95 | 7.06 | 0.84 |
| Example 21 | 268.50 | 4.43 | 19.77 | 0.35 |

INDUSTRIAL APPLICABILITY

The sustained-release composition of the present invention can contain a high content of a physiologically active substance and suppress the initial excessive release thereof and enable a long-term stable release rate.

That is, the suppression of the initial excessive release of the physiologically active peptide and the stable release of the drug on onset part after administration can be achieved, additionally, the sustained-release composition of the present invention can stably sustained-release the physiologically active substance for a long period from about 60 to 400 days after the administration at the effective blood concentration.

Additionally, since a content of a physiologically active substance in the preparation is higher than that of the conventional preparation, a volume and weight of whole sustained-release preparation needed per unit dose of the active ingredient can be reduced. Thereby, the physical burden can be relieved in patients such as a pain at the time of administration and an induration after administration considered due to administration of a preparation having a large unit volume.

The invention claimed is:

1. A method for treating prostate cancer, prostatic hyperplasia, endometriosis, uterine fibroid, uterine fibroma, precocious puberty, dysmenorrhea, or breast cancer, or a method of contraception, comprising administering to a mammal an effective amount of a sustained-release composition in which a physiologically active substance, which is a peptide of formula: 5-oxo-Pro-His-Trp-Ser-Tyr-DLeu-Leu-Arg-Pro-NH—$C_2H_5$ or an acetate thereof, is substantially uniformly dispersed in a microcapsule comprised of a lactic acid polymer or a salt thereof, wherein the physiologically active substance is contained in an amount of 15 to 35 (weight/weight) % to the total microcapsules, weight-average molecular weight (Mw) of the lactic acid polymer is about 11,000 to about 27,000, and the sustained-release composition further contains stearic acid.

2. The method according to claim 1, wherein the weight-average molecular weight (Mw) of the lactic acid polymer is any one selected from:
(i) about 11,600 to about 20,000 and
(ii) about 19,000 to about 27,000.

3. The method according to claim 2 wherein the weight-average molecular weight (Mw) of the lactic acid polymer is (i) about 11,600 to about 20,000, and the sustained-release composition comprises maintaining an effective drug blood level over a period of about 60 days to 130 days by in vivo release of the physiologically active substance from the sustained-release composition.

4. The method according to claim 2 wherein the weight-average molecular weight (Mw) of the lactic acid polymer is (ii) about 19,000 to about 27,000, and the sustained-release composition comprises maintaining an effective drug blood level over a period of about 120 days to 400 days by in vivo release of the physiologically active substance from the sustained-release composition.

5. The method according to claim 1, wherein a ratio of stearic acid to the total microcapsules is about 0.01 to about 50% by weight.

6. The method according to claim 1, wherein an amount of stearic acid to be added is 0.1 to 10 moles relative to one mole of the water-soluble physiologically active peptide or the salt thereof.

7. The method according to claim 1, wherein the sustained-release composition is easily dispersible in a disperse medium.

8. The method according to claim 7, wherein the sustained-release composition is stable for 24 hours or more after dispersion in the disperse medium.

9. The method according to claim 2 wherein the weight-average molecular weight (Mw) of the lactic acid polymer is (i) about 11,600 to about 20,000, which is characterized in that a ratio of the weight-average molecular weight (Mw) to the number-average molecular weight (Mn) is more than 1.9.

10. The method according to claim 2 wherein the weight-average molecular weight (Mw) of the lactic acid polymer is (ii) about 19,000 to about 27,000, which is characterized in that a ratio of the weight-average molecular weight (Mw) to the number-average molecular weight (Mn) is more than 1.5.

11. The method according to claim 1, wherein the lactic acid polymer is polylactic acid.

12. The method according to claim 1, wherein the lactic acid polymer is poly-DL-lactic acid.

13. The method according to claim 1, wherein the lactic acid polymer is a lactic acid-glycolic acid polymer.

14. The method according to claim 13, wherein a composition ratio of lactic acid/glycolic acid in the lactic acid-glycolic acid polymer is 60/40 to 99.9/0.1.

15. The method according to claim 1, wherein the lactic acid polymer is a polymer containing a polymer having a molecular weight of 5,000 or less whose content is about 5.0% by weight or less.

16. The method according to claim 1, wherein the lactic acid polymer is a polymer containing a polymer having a molecular weight of 3,000 or less whose content is about 1.5% by weight or less.

17. The method according to claim 1, wherein the lactic acid polymer is a polymer containing a polymer having a molecular weight of 1,000 or less whose content is about 0.1% by weight or less.

18. The method according to claim 2 in which the weight-average molecular weight (Mw) of the lactic acid polymer is 12,000 to 19,000.

19. The method according to claim 2 in which the weight-average molecular weight (Mw) of the lactic acid polymer is 13,000 to 18,000.

20. The method according to claim 2 in which the weight-average molecular weight (Mw) of the lactic acid polymer is 19,500 to 26,500.

21. The method according to claim 2 in which the weight-average molecular weight (Mw) of the lactic acid polymer is (i) about 11,600 to about 20,000, and the sustained-release composition is characterized in that a ratio of a maximum blood concentration of a physiologically active substance within 24 hours after the administration to an average blood concentration of the physiologically active substance for a period from 24 hours to one month after the administration is 2 to 50.

22. The method according to claim 2 in which the weight-average molecular weight (Mw) of the lactic acid polymer is (i) about 11,600 to about 20,000, and the sustained-release composition is characterized in that a ratio of a maximum blood concentration of a physiologically active substance within 24 hours after the administration to an average blood concentration of the physiologically active substance for a period from one month to three months after the administration is 20 to 350.

23. The method according to claim 2 in which the weight-average molecular weight (Mw) of the lactic acid polymer is (i) about 11,600 to about 20,000, and the sustained-release composition is characterized in that area under the blood concentration-time curve (AUC) of a physiologically active substance within 24 hours after the administration calculated from the blood concentration is 3% to 30% of the whole AUC.

24. The method according to claim 2 in which the weight-average molecular weight (Mw) of the lactic acid polymer is (ii) about 19,000 to about 27,000, and the sustained-release composition is characterized in that a ratio of a maximum blood concentration of a physiologically active substance within 24 hours after the administration to an average blood concentration of the physiologically active substance for a period from 24 hours to one month after the administration is 10 to 90.

25. The method according to claim 2 in which the weight-average molecular weight (Mw) of the lactic acid polymer is (ii) about 19,000 to about 27,000, and the sustained-release composition is characterized in that a ratio of a blood maximum concentration of a physiologically active substance within 24 hours after the administration to an average blood concentration of the physiologically active substance for a period from one month to six months after the administration is 20 to 500.

26. The method according to claim 2 in which the weight-average molecular weight (Mw) of the lactic acid polymer is (ii) about 19,000 to about 27,000, and the sustained-release composition is characterized in that area under the blood concentration-time curve (AUC) of a physiologically active substance within 24 hours after the administration calculated from the blood concentration is 1% to 20% of the whole AUC.

27. A method for reducing premenopausal breast cancer postoperative recurrence, comprising administering to a mammal an effective amount of a sustained-release composition in which a physiologically active substance, which is a peptide of formula: 5-oxo-Pro-His-Trp-Ser-Tyr-DLeu-Leu-Arg-Pro-NH—$C_2H_5$ or an acetate thereof, is substantially uniformly dispersed in a microcapsule comprised of a lactic acid polymer or a salt thereof, wherein the physiologically active substance is contained in an amount of 15 to 35 (weight/weight) % to the total microcapsules, and weight-average molecular weight (Mw) of the lactic acid polymer is about 11,000 to about 27,000 and the sustained-release composition further contains stearic acid.

* * * * *

UNITED STATES PATENT AND TRADEMARK OFFICE
CERTIFICATE OF CORRECTION

PATENT NO.        : 9,617,303 B2                                               Page 1 of 1
APPLICATION NO.   : 14/547467
DATED             : April 11, 2017
INVENTOR(S)       : Futo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 96 days.

Signed and Sealed this

Twenty-fifth Day of September, 2018

Andrei Iancu
*Director of the United States Patent and Trademark Office*